(12) United States Patent
Scheibel et al.

(10) Patent No.: US 6,602,840 B1
(45) Date of Patent: *Aug. 5, 2003

(54) PROCESSES FOR MAKING ALKYLBENZENESULFONATE SURFACTANTS AND PRODUCTS THEREOF

(75) Inventors: Jeffrey John Scheibel, Loveland, OH (US); Kevin Lee Kott, Loveland, OH (US); Thomas Anthony Cripe, Loveland, OH (US); James Charles Theophile Roger Burckett-St. Laurent, Cincinnati, OH (US); Daniel Stedman Connor, Cincinnati, OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/478,909

(22) Filed: Jan. 7, 2000

Related U.S. Application Data

(63) Continuation of application No. PCT/IB98/01096, filed on Jul. 20, 1998.
(60) Provisional application No. 60/053,209, filed on Jul. 21, 1997.

(51) Int. Cl.$^7$ .............................................. C11D 17/00
(52) U.S. Cl. .................... 510/357; 510/424; 510/426; 510/428; 510/492
(58) Field of Search ................................. 510/424, 426, 510/428, 357, 492

(56) References Cited

U.S. PATENT DOCUMENTS

| | | | |
|---|---|---|---|
| 2,477,382 A | 7/1949 | Lewis | 260/671 |
| 2,564,072 A | 8/1951 | Lien et al. | 260/671 |
| 3,196,174 A | 7/1965 | Cohen | 260/505 |

(List continued on next page.)

FOREIGN PATENT DOCUMENTS

| | | | |
|---|---|---|---|
| AU | 39394/89 | 2/1990 | ............ C07C/2/02 |
| CA | 2201953 | 10/1997 | ............ C07C/5/27 |
| DE | 42 24 947 | 2/1994 | ........... C11D/3/386 |
| DE | 42 36 698 | 2/1994 | ........... C11D/3/386 |
| EP | 0 321 177 | 6/1989 | ........... C01B/33/34 |

(List continued on next page.)

OTHER PUBLICATIONS

"Petroleum–Based Raw Materials for Anionic Surfactants", Surfactant Science Series, vol. 7, Part 1, Chapter 2, pp. 11–86, Ed. W. M. Linfield, Marcel Dekker, Inc., New York (1996), * NMA.

(List continued on next page.)

*Primary Examiner*—Necholus Ogden
(74) *Attorney, Agent, or Firm*—Ian S. Robinson; Kim W. Zerby; Steven W. Miller

(57) ABSTRACT

The present invention is in the field of processes for making alkylbenzenesulfonate surfactants. The processes herein include a combination of two essential steps, delinearization and alkylation. The delinearization step selected herein introduces particular types of limited branching into an aliphatic hydrocarbon having ten or more, but no more than about 16, carbon atoms. The hydrocarbon includes olefin having a hydrocarbon chain length suitable for detergent manufacture, e.g., $C_{10}$–$C_{14}$, or a corresponding paraffin. The second essential step is an alkylation step having an internal isomer selectivity of from 0 to no more than about 40 in which the hydrocarbon is used to monoalkylate benzene catalytically with an alkylation catalyst. Such alkylation catalysts preferably comprise an at least partially crystalline porous zeolite-containing solid, the zeolite having moderate acidity and intermediate pore size. Preferred alkylation catalysts include certain at least partially dealuminized acidic nonfluoridated mordenites. The processes herein further comprise sulfonating, neutralizing and incorporating the resulting modified alkylbenzenesulfonate surfactants into consumer products. The invention relates also to the products of the processes, including modified surfactants and consumer cleaning products containing them.

50 Claims, 5 Drawing Sheets

U.S. PATENT DOCUMENTS

| | | | |
|---|---|---|---|
| 3,238,249 A | 3/1966 | Mirviss et al. | 260/505 |
| 3,312,745 A | 4/1967 | Habeshaw et al. | 260/638 |
| 3,341,614 A | 9/1967 | Wirth et al. | 260/671 |
| 3,351,654 A | 11/1967 | Gudelis | 260/505 |
| 3,355,484 A | 11/1967 | Bloch | 260/505 |
| 3,427,342 A | 2/1969 | Brooks et al. | 260/458 |
| 3,442,964 A | 5/1969 | Oldham | 260/671 |
| 3,442,965 A | 5/1969 | Oldham | 260/671 |
| 3,491,030 A | 1/1970 | Fields | 252/161 |
| 3,492,364 A | 1/1970 | Jones et al. | 260/671 |
| 3,562,797 A | 2/1971 | Hu | 260/683.3 |
| 3,674,885 A | 7/1972 | Griesinger et al. | 260/671 |
| 4,235,810 A | 11/1980 | Osselet et al. | 260/505 |
| 4,259,193 A | 3/1981 | Tirtiaux et al. | 252/33 |
| 4,301,316 A | 11/1981 | Young | 585/455 |
| 4,301,317 A | 11/1981 | Young | 585/455 |
| 4,447,664 A | 5/1984 | Murchison et al. | 585/323 |
| 4,533,651 A | 8/1985 | Masters et al. | 502/117 |
| 4,587,374 A | 5/1986 | Peters | 585/670 |
| 4,645,623 A | 2/1987 | Dolan et al. | 252/558 |
| 4,731,497 A | 3/1988 | Grey | 585/455 |
| 4,855,527 A | 8/1989 | Page et al. | 585/527 |
| 4,870,038 A | 9/1989 | Page et al. | 502/62 |
| 4,959,491 A | 9/1990 | Threlkel | 562/94 |
| 4,962,256 A | 10/1990 | Le et al. | 585/467 |
| 4,973,788 A | 11/1990 | Lin et al. | 585/511 |
| 4,990,718 A | 2/1991 | Pelrine | 585/455 |
| 4,996,386 A | 2/1991 | Hamilton, Jr. et al. | 585/646 |
| 5,026,933 A | 6/1991 | Blain et al. | 585/7 |
| 5,030,785 A | 7/1991 | Huss, Jr. et al. | 585/456 |
| 5,087,788 A | 2/1992 | Wu | 585/512 |
| 5,146,026 A | 9/1992 | Berna Tejero et al. | 585/467 |
| 5,177,280 A | 1/1993 | Juguin et al. | 585/323 |
| 5,196,574 A | 3/1993 | Kocal | 562/94 |
| 5,196,624 A | 3/1993 | Threlkel et al. | 585/513 |
| 5,196,625 A | 3/1993 | Threlkel et al. | 585/513 |
| 5,198,595 A | 3/1993 | Lee et al. | 585/467 |
| 5,210,060 A | 5/1993 | Radlowski et al. | 502/202 |
| 5,243,116 A | 9/1993 | Lee et al. | 585/467 |
| 5,245,072 A | 9/1993 | Giacobbe et al. | 560/99 |
| 5,246,566 A | 9/1993 | Miller | 208/27 |
| 5,258,566 A | 11/1993 | Kresge et al. | 585/467 |
| 5,302,732 A | 4/1994 | Steigleder et al. | 554/98 |
| 5,326,928 A | 7/1994 | Benazzi et al. | 585/820 |
| 5,334,793 A | 8/1994 | Kocal | 585/323 |
| 5,344,997 A | 9/1994 | Kocal | 568/628 |
| 5,401,896 A | 3/1995 | Kuehl et al. | 585/455 |
| 5,491,271 A | 2/1996 | Marinangeli et al. | 585/468 |
| 5,510,306 A | 4/1996 | Murray | 502/64 |
| 5,602,292 A | 2/1997 | Perego et al. | 585/750 |
| 5,625,105 A | 4/1997 | Lin et al. | 585/511 |
| 5,811,612 A | 9/1998 | Girotti et al. | 585/467 |
| 5,811,623 A | 9/1998 | Ryu et al. | 585/671 |

FOREIGN PATENT DOCUMENTS

| | | | |
|---|---|---|---|
| EP | 0 364012 | 4/1990 | C07C/303/24 |
| EP | 0 466558 | 1/1992 | C07C/15/107 |
| EP | 0 469940 | 2/1992 | C07C/15/107 |
| EP | 0 807 616 | 11/1997 | C07C/2/70 |
| FR | 2697246 | 4/1994 | C07C/15/107 |
| GB | 936 882 | 9/1963 | |
| GB | 2 083 490 | 3/1982 | |
| GB | 2 278 125 | 11/1994 | C11D/1/12 |
| SU | 793972 | 1/1981 | C07C/2/22 |
| WO | WO 88/07030 | 9/1988 | C07C/2/32 |
| WO | WO 95/17961 | 7/1995 | B01J/29/06 |
| WO | WO 95/18084 | 7/1995 | C07C/5/27 |
| WO | WO 95/21225 | 8/1995 | C09K/7/00 |
| WO | WO 97/01521 | 1/1997 | C07C/1/04 |
| WO | WO 97/29063 | 8/1997 | C07C/15/107 |
| WO | WO 97/29064 | 8/1997 | C07C/15/107 |
| WO | WO 97/47573 | 12/1997 | C07C/2/66 |

OTHER PUBLICATIONS

Nooi, J. R., et al., "Isomerization Reactions Occurring on Alkylation of Benzene with Some Branched Long–Chain 1–Alkenes", RECUEIL, vol. 88, No. 4, pp. 398–410 (1969), *NMA.

Research Disclosure No. 41412, "Hydrocarbon Mixture", Research Disclosure, vol. 414 (Oct. 1998).

U.S. patent application Ser. No. 09/479,369, Scheibel et al., filed Jan. 7, 2002.

U.S. patent application Ser. No. 09/478,908, Scheibel et al., filed Jan. 7, 2000.

U.S. patent application Ser. No. 09/479,365, Kott et al., filed Jan. 7, 2000.

U.S. patent application Ser. No. 09/478,909, Scheibel et al., filed Jan. 7, 2000.

U.S. patent application Ser. No. 09/479,364, Connor et al., filed Jan. 2000.

PROCESSES FOR MAKING ALKYLBENZENESULFONATE SURFACTANTS AND PRODUCTS THEREOF

CROSS REFERENCE

This is a continuation under 35 USC §120 of PCT International Application Serial No. PCT/IB98/01096, filed Jul. 20, 1998; which claims priority to Provisional Application Ser. No. 60/053,209, filed Jul. 21, 1997.

FIELD OF THE INVENTION

The present invention is in the field of processes for making alkylbenzenesulfonate surfactants. The processes herein include a combination of two essential steps, delinearization and alkylation. The delinearization step selected herein introduces particular types of limited branching into an aliphatic hydrocarbon having ten or more, but no more than about 16, carbon atoms. The hydrocarbon includes olefin having a hydrocarbon chain length suitable for detergent manufacture, e.g., $C_{10}$–$C_{14}$, or a corresponding paraffin. The second essential step is an alkylation step having an internal isomer selectivity of from 0 to no more than about 40 in which the hydrocarbon is used to monoalkylate benzene catalytically with an alkylation catalyst. Such alkylation catalysts preferably comprise an at least partially crystalline porous zeolite-containing solid, the zeolite having moderate acidity and intermediate pore size. Preferred alkylation catalysts include certain at least partially dealuminized acidic nonfluoridated mordenites. The processes herein further comprise sulfonating, neutralizing and incorporating the resulting modified alkylbenzenesulfonate surfactants into consumer products. The invention relates also to the products of the processes, including modified surfactants and consumer cleaning products containing them.

BACKGROUND OF THE INVENTION

Historically, highly branched alkylbenzenesulfonate surfactants, such as those based on tetrapropylene (known as "ABS" or "TPBS") were used in detergents. However, these were found to be very poorly biodegradable. A long period followed of improving manufacturing processes for alkylbenzenesulfonates, making them as linear as practically possible ("LAS"). The overwhelming part of a large art of linear alkylbenzenesulfonate surfactant manufacture is directed to this objective. Large-scale commercial alkylbenzenesulfonate processes in use in the U.S. today are directed to linear alkylbenzenesulfonates. However, linear alkylbenzenesulfonates are not without limitations; for example, they would be more desirable if improved for hard water and/or cold water cleaning properties.

In the petroleum industry, various processes have more recently been developed, for example for producing low viscosity lube oil, which the inventors have now discovered provide new insight on how to delinearize hydrocarbons to a limited and controlled extent. Such deliberate delinearization, however, is not a feature of any current commercial processes in the different field of alkylbenzenesulfonate surfactant manufacture for consumer products. This is not surprising, in view of the overwhelming volume of LAS surfactant art teaching toward linear compounds and away from delinearization.

The majority of commercial processes for making alkylbenzenes rely on HF or aluminum chloride catalyzed alkylation of benzene. Quite recently, it has been discovered that certain zeolite catalysts can be used for alkylation of benzene with olefins. Such a process step has been described in the context of otherwise conventional processes for manufacture of linear alkylbenzenesulfonates. For example, the DETAL® process of UOP uses a zeolite alkylation catalyst. The DETAL® process and all other current commercial processes for alkylbenzenesulfonate manufacture are believed to fail to meet the internal isomer selectivity requirements of the inventive process and alkylation catalyst defined hereinafter. Moreover, the DETAL® process catalyst or catalysts are believed to lack the moderate acidity and intermediate pore size of alkylation catalysts used in the processes of the present invention. Other recent literature describes the use of mordenite as an alkylation catalyst, but no such disclosure makes the combination of specific process steps required by the instant invention. Moreover, in view of the linearity desired in alkylbenzenesulfonate products of conventionally known processes, they also generally include steps directed to the provision or making of a substantially linear hydrocarbon, not a delinearized one, prior to the alkylation. A possible exception is in U.S. Pat. No. 5,026,933 which includes, for example, oligomerization of lower olefin such as propylene under narrowly defined conditions using collidine-deactivated ZSM-23 to form a composition comprising a tetramer assertedly having 1.3 methyl branches per chain, followed by fractionation and an alkylation using mordenite catalyst. See Example XVII. See also U.S. Pat. No. 4,990,718 in which an alkylbenzene is made via a process that produces a vinylidene olefin by dimerization in presence of chromium catalyst but in which the vinylidene yield is adversely affected by oligomerization and in which distillation is required prior to alkylation. However, the processes of '933 and '718 have numerous shortcomings from the standpoint of the detergent industry in terms of cost, catalyst limitations in the propylene oligomerization or olefin dimerization stage, presence of large volumes of distillation fractions that would need to be discarded or find nondetergent customers, and limited range of product compositions, including mixtures of chainlengths attainable. Such developments by the petroleum industry are, in short, not optimal from the standpoint of the expert formnulator of detergent products.

BACKGROUND ART

U.S. Pat. No. 5,026,933; U.S. Pat. No. 4,990,718; U.S. Pat. No. 4,301,316; U.S. Pat. No. 4,301,317; U.S. Pat. No. 4,855,527; U.S. Pat. No. 4,870,038; U.S. Pat. No. 2,477,382; EP 466,558, Jan. 15, 1992; EP 469,940, Feb. 5, 1992; FR 2,697,246, Apr. 29, 1994; SU 793,972, Jan. 7, 1981; U.S. Pat. No. 2,564,072; U.S. Pat. No. 3,196,174; U.S. Pat. No. 3,238,249; U.S. Pat. No. 3,355,484; U.S. Pat. No. 3,442,964; U.S. Pat. No. 3,492,364; U.S. Pat. No. 4,959,491; WO 88/07030, Sep. 25, 1990; U.S. Pat. No. 4,962,256, U.S. Pat. No. 5,196,624; U.S. Pat. No. 5,196,625; EP 364,012 B, Feb. 15, 1990; U.S. Pat. No. 3,312,745; U.S. Pat. No. 3,341,614; U.S. Pat. No. 3,442,965; U.S. Pat. No. 3,674,885; U.S. Pat. No. 4,447,664; U.S. Pat. No. 4,533,651; U.S. Pat. No. 4,587,374; U.S. Pat. No. 4,996,386; U.S. Pat. No. 5,210,060; WO 95/17961, Jul. 6, 1995; WO 95/18084; U.S. Pat. No. 5,510,306; U.S. Pat. No. 5,087,788; U.S. Pat. No. 5,625,105 and U.S. Pat. No. 4,973,788 are useful by way of background to the invention. The manufacture of alkylbenzenesulfonate surfactants has recently been reviewed. See Vol. 56 in "Surfactant Science" series, Marcel Dekker, New York, 1996, including in particular Chapter 2 entitled "Alkylarylsulfonates: History, Manufacture, Analysis and Environmental Properties", pages 39–108 which includes 297 literature references. Documents referenced herein are incorporated in their entirety.

SUMMARY OF THE INVENTION

The present invention is predicated on an unexpected discovery that combining a specifically defined delinearization step or steps of a non-lower olefin or paraffin ("non-lower" meaning having 10 or more carbon atoms) with a particularly defined selective alkylation step results in an unexpectedly superior alkylbenzenesulfonate surfactant product.

Accordingly, in one aspect, the present invention relates to a process for preparing modified alkylbenzenesulfonate surfactant suitable for use in cleaning products such as laundry detergents, hard surface cleaners, dishwashing detergents and the like, said process comprising (a) reducing the linearity of an olefin, preferably one having molecular weight of at least about 126 and no more than about 280, preferably no more than about 224, by a step of skeletally isomerizing, in the presence of a constrained skeletal isomerization catalyst, a substantially linear olefin preformed to have at least said molecular weight; and (b) a monoalkylation step having low internal isomer selectivity (from 0 to no more than 40 preferably from 0 to no more than 20, more preferably from 0 to no more than 10 using measures further defined hereinafter), of reacting the product of step (a) with an aromatic hydrocarbon selected from benzene, toluene and mixtures thereof in the presence of a particularly defined alkylation catalyst. Such catalyst comprises a moderate acidity, medium-pore zeolite defined in detail hereinafter. A particularly preferred alkylation catalyst comprises at least partially dealuminized acidic nonfluoridated mordenites.

In another aspect, the invention relates to a process for preparing modified alkylbenzenesulfonate surfactant suitable for use in cleaning products, said process comprising (a) a step of arriving at (making or providing) a reduced-linearity alkylating agent selected from an olefin having molecular weight, n, of at least about 126 and no more than about 280 and produced by a sequence of steps comprising: (i) skeletally isomerizing a linear paraffin having molecular weight of n+2 where n is said molecular weight of said olefin; and (ii) dehydrogenating the isomerized paraffin; and (b) a monoalkylation step of reacting the reduced-linearity alkylation agent of stage (a) (that is, the hydrocarbon produced in that stage) with an aromatic hydrocarbon selected from benzene, toluene and mixtures thereof in the presence of an alkylation catalyst identical with that which is used in the embodiment described in the preceding paragraph.

The invention also encompasses a process according to either of the foregoing aspects or embodiments of the invention having the additional steps, of (c) sulfonating the product of step (b); and one or more steps selected from (d) neutralizing the product of step (c); and (e) mixing the product of step (c) or (d) with one or more cleaning product adjunct materials; thereby forming a cleaning product.

Moreover the invention also encompasses cleaning products including heavy-duty and light-duty laundry detergents, hard surface cleaners, dishwashing detergents, laundry bars, detergent tablets or detergent gels, shampoos and the like formed by any of the processes described.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

Processes with Reference to the Drawings

Figure 1:
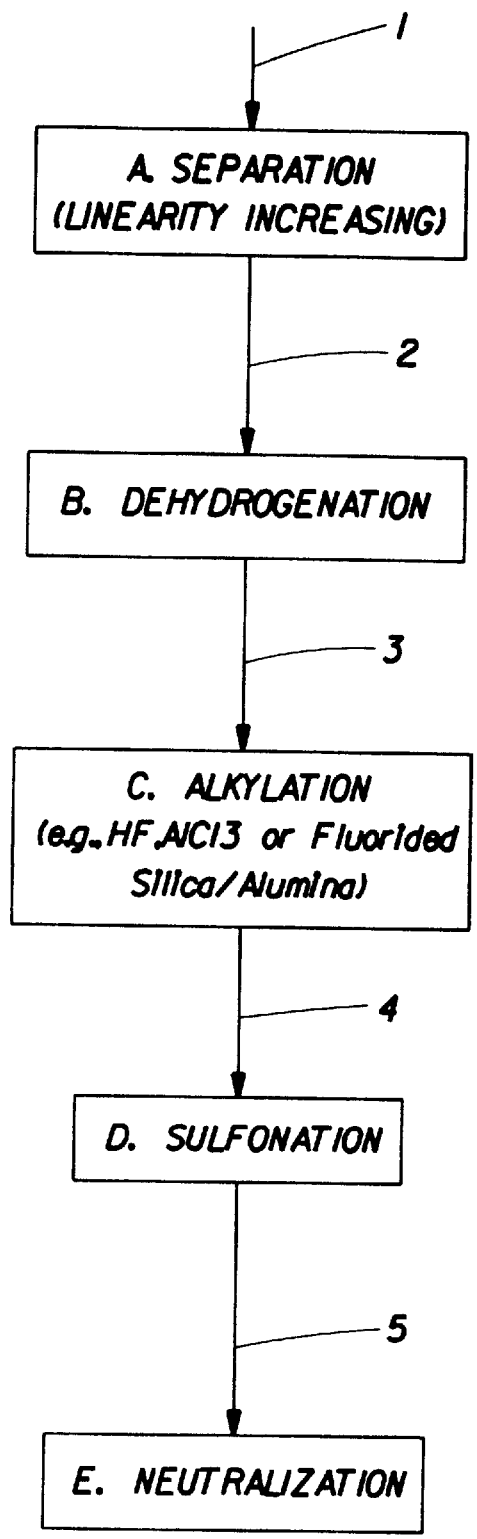
FIG. 1 is a block diagram of a conventional commercial process for the manufacture of linear alkylbenzenesulfonate surfactants.
Figure 2:
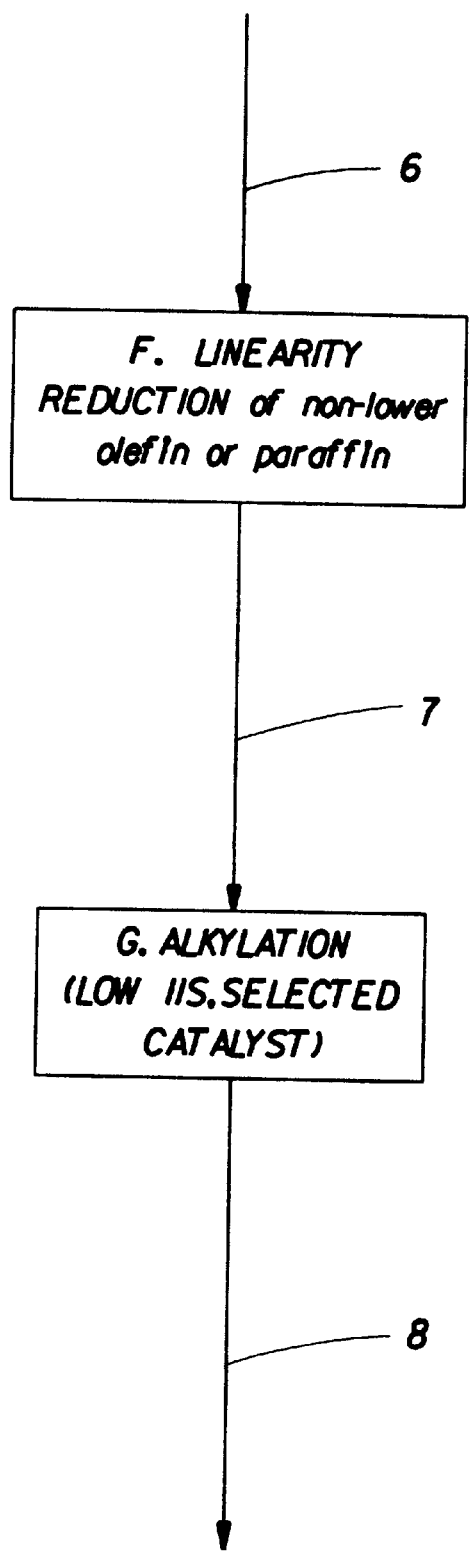
FIGS. 2 to 4 are block diagrams of processes according to the invention.
Figure 3:
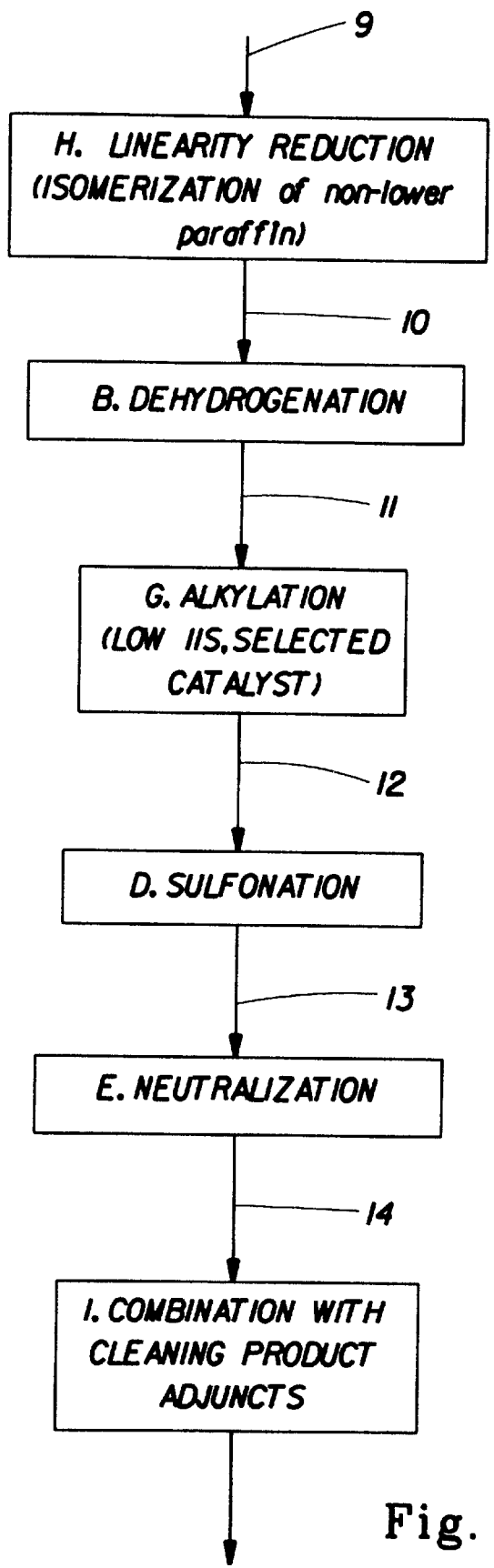
Figure 4:
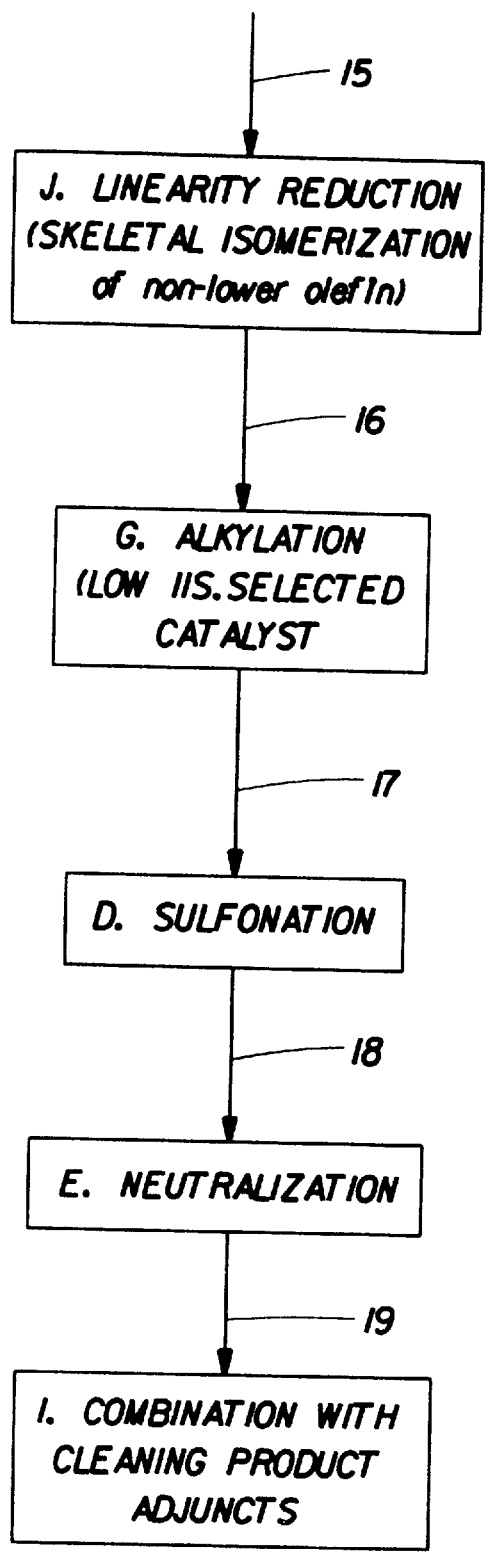
Figure 5:
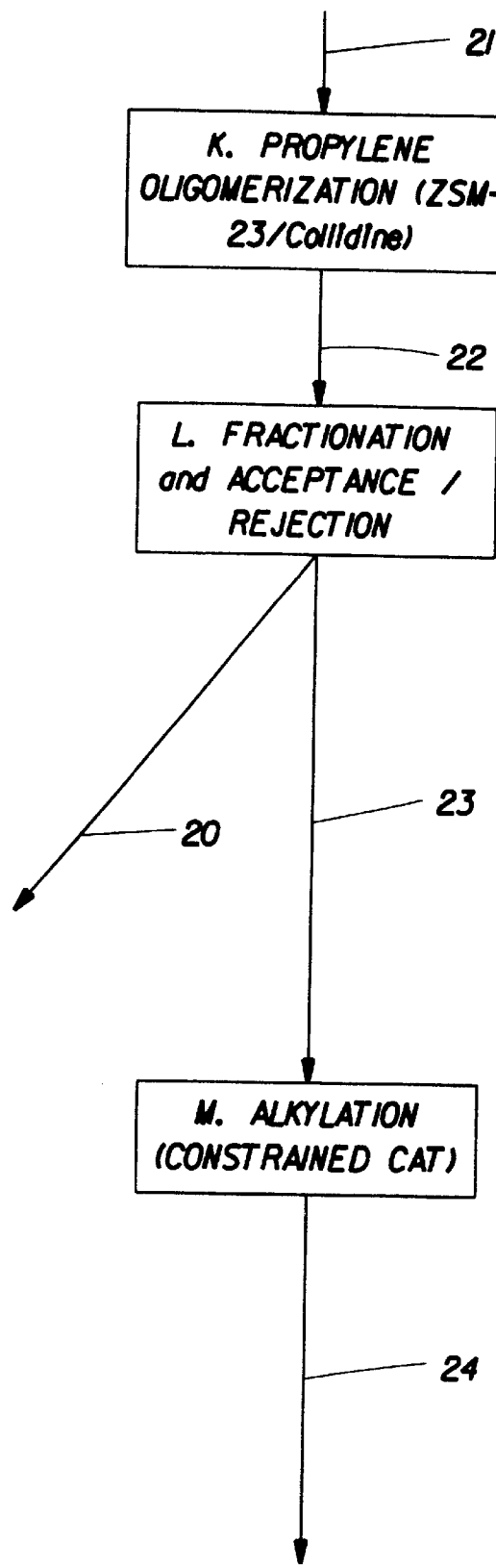
FIG. 5 is a block diagram of a literature process. Capital letters, e.g., A, B, C, are used to denote steps in these processes. Numbers such as 1, 2, 3, refer to compositions input and/or output from the process steps.

The processes of the present invention will be better understood with reference to FIGS. 1 to 5. As noted, FIG. 1 is a block diagram of a conventional commercial process for the manufacture of linear alkylbenzenesulfonate surfactants. FIGS. 2 to 4 are block diagrams of processes according to the invention. FIG. 5 is a block diagram of a literature process.

For purposes of comparison with the process of the present invention, a conventional commercial process for making LAS, for example from kerosene or other paraffins, includes the steps A–E in FIG. 1. Based on the conventional wisdom that substantial linearity (generally >90%, commonly >95%) is essential, efforts are generally made to provide a linear feedstock or increase the linearity of the feedstock, for example using the MOLEX® sieving process of UOP to remove branched paraffins. In FIG. 1 input stream 1 is typically kerosene. The product of step A, namely 2 in FIG. 1, is a linear or substantially linear paraffin, commonly $C_{10}$–$C_{14}$ linear paraffin. Step B, a dehydrogenation step, in commercial practice is commonly the PACOLO® process of UOP optionally complemented by the DEFINE® process of UOP (the DEFINE® process converting any dienes in the feed to monoolefins), and produces linear or substantially linear monoolefins as output 3. The linear olefins are alkylated, typically using HF or aluminum chloride in step C though more recently, improvements on the HF process take the form of liquid phase alkylation steps using a fluorided, amorphous silica/alumina catalyst. Such processes include the DETAL® process of UOP and CEPSA (Petresa) and processes described in U.S. patents such as U.S. Pat. No. 5,344,997, U.S. Pat. No. 5,196,574 and U.S. Pat. No. 5,334,793. See also U.S. Pat. No. 5,245,094. The product alkylbenzenes, 4, are sulfonated D and the alkylbenzene sulfonic acids produced, 5, are neutralized E. Sulfonation and neutralization steps can take place in a facility remote from that used to produce the linear alkylbenzene (LAB) A–C.

With reference to the process in FIG. 2, the process of the present invention, surprisingly, is required to have a linearity reduction or delinearization step, wherein the delinearization is applied to a non-lower olefin or non-lower paraffin feed, 6. This step is shown as step F in FIG. 2 and exemplified in FIGS. 3–4 by specific steps H and J for introducing limited branching into the non-lower feed olefin or paraffin (identified as 9 and 15 in FIGS. 3–4). Further, the inventive process is required to have a step, shown as step G in FIGS. 2–4, of alkylating hydrocarbon (identified as 7, 11, and 16 in FIGS. 2–4), with an alkylation catalyst defined at length hereinafter. Such catalyst herein is generally at least partially crystalline (it is not amorphous) and is unreliant on HF or its derivatives (including fluorided silica/alumina) or aluminum chlorides which are strongly acidic and/or give otherwise compositionally unacceptable products. The catalytic alkylation step herein more particularly can use a specifically selected zeolite further described and illustrated hereinafter. The modified alkylbenzene (MAB) produced in processes shown in FIGS. 2–4 and shown as 8, 12, 13, 17 and 18, is sulfonated and neutralized by individually known steps shown as D and E. In preferred processes, an additional step, (shown in FIGS. 3–4 as 14 and 19) is used to combine the sulfonated MAB with detergent adjuncts to produce novel consumer cleaning products, shown in step I.

Step B, a dehydrogenation step, in the process of FIG. 3 produces linearity reduced or delinearizatized monoolefins as output 10.

Processes shown in the drawings, whether they be conventional and commercially practiced, e.g., FIG. 1, or known from the literature, e.g., FIG. 5, or novel, e.g., in FIGS. 2–4, can include any additional steps not shown in the figures but known in the art. Such steps can be inserted between steps shown in the figures. Such steps include, for example, passage of an intermediate stream through a sorptive separation zone using nonacidic zeolites to limit dialkyl tetralins in the feed for the alkylation. See, for example, U.S. Pat. No. 2,276,231. Other such steps include the common steps of distilling the alkylbenzenes.

The process shown as FIG. 5 as noted reproduces an art-known process, that of U.S. Pat. No. 5,026,933, for purposes of comparison. The process of U.S. Pat. No. 5,026,933 is not known to be in commercial use. Notable shortcomings of this process beyond its assumed lack of successful commercial exploitation include that it is limited to lower olefin feedstocks, shown as 21, specifically propylene and/or butylene (step K in FIG. 5); fractionation is required, shown as 22, (step L in FIG. 5) and there are large proportions of rejects not useful for making cleaning surfactants, shown as 20. Note that oligomerization of propylene and/or butylene or other "lower" olefins as defined herein are not practiced in the essential steps of the present inventive processes. The nonreject stream, 23, is then reacted with an aromatic hydrocarbon in the presence of a constrained alkylation catalyst, (step M, in FIG. 5) producing a linear alkyl aromatic, 24.

Processes in More Detail

As noted in summary, the present invention relates to a process for preparing modified alkylbenzenesulfonate surfactant suitable for use in cleaning products such as laundry detergents, hard surface cleaners, dishwashing detergents and the like.

The term "modified alkylbenzenesulfonate surfactant" (MAS) refers to the product of the processes herein. The term "modified" as applied either to the novel alkylbenzenesulfonate surfactants or to the novel alkylbenzenes (MAB) is used as a qualifier to indicate that the product of the present process is compositionally different from that of all alkylbenzenesulfonate surfactants hitherto used in commerce. Most particularly, the instant compositions differ compositionally from the so-called "ABS" or poorly biodegradable alkylbenzenesulfonates, and from the so-called "LAS" or linear alkylbenzenesulfonate surfactants. Conventional LAS surfactants are currently commercially available through several processes including those relying on HF-catalyzed or aluminum chloride-catalyzed alkylation of benzene. Other commercial LAS surfactants include LAS made by the DETAL® process. The modified alkylbenzenesulfonate surfactants herein are also compositionally different from those made by alkylating linear olefins using fluoridated zeolite catalyst systems, including fluoridated mordenites. Without being limited by theory, it is believed that the modified alkylbenzenesulfonate surfactants herein are uniquely lightly branched. They typically contain a plurality of isomers and/or homologs. Often, this plurality of species (often tens or even hundreds) is accompanied by a relatively high total content of 2-phenyl isomers, 2-phenyl isomer contents at the very least exceeding current DETAL® process and commonly 50% or even 70% or higher being attained. Moreover the modified alkylbenzenesulfonate products herein differ in physical properties from known alkylbenzenesulfonate surfactants, for example by having improved laundry/hard surface cleaning performance and excellent mass efficiency in hard water.

The invention includes a process comprising (a) reducing the linearity of an olefin, preferably one having molecular weight of at least about 126 and no more than about 280. Typical olefin molecular weight range for olefin feedstock in preferred processes can be as limited as from about 140 to about 196. Reducing linearity or "delinearization" contradicts most recent developments in alkylbenzenesulfonate detergent manufacture, which are directed to increasing linearity based on the notion (which the inventors believe is incorrect) that only strict linearity will guarantee environmental compatibility. Of the essence in the present invention is the notion that linearity reduction processing, if combined with a particular type of alkylation later in the process, is not necessarily incompatible with maintaining biodegradability and can at the same time lead to important compositional advantages, in performance or end-result terms, of the modified alkylbenzenesulfonate product and consumer products containing it.

The opportunity to achieve a meaningful improvement by delinearization or light branching in alkylbenzenesulfonate surfactants appears technically to be very limited. This is at least partially on account of the rather restricted range of total carbon content which is necessary for good surfactancy and good solubility in this particular type of surfactant. Most current LAS, to be useful, is based on a range as narrow as from about C10 to about C14 for the alkyl portion of the alkylbenzenesulfonate molecule. Delinearizing the surfactant while remaining in this narrow range of overall carbon content might be expected to worsen the surfactancy performance even if it improved another physical property.

Linearity reduction herein in one important mode is generally accomplished by a step selected from: skeletally isomerizing, in the presence of a constrained skeletal isomerization catalyst, a substantially linear olefin preformed to have at least said molecular weight.

Linearity Reduction via Skeletal Isomerization of Olefin

Preferred starting-material olefins for delinearization of olefins by skeletal isomerization herein are alpha-olefins having the required molecular weight. Suitable olefins can in general be obtained from any source. Such olefins include those made by dehydrogenation of a linear paraffin, including especially those made from kerosene processed through the PACOL™ and OLEX™ processes of UOP or less preferably via the old Shell (CDC) process; alpha-olefins generated by ethylene polymerization, for example by the Shell, Gulf/Chevron, or Amoco (formerly Ethyl Corp.) processes; alpha olefins derived from cracked wax; alpha-olefins derived from Fischer-Tropsch syntheses, or internal olefins from Shell's SHOP™ process. As used, the olefins can contain varying amounts of non-monoolefinic material, such as paraffins, as long as such materials do not materially interfere with the skeletal isomerization step. If olefin raw materials contain unacceptable impurities, such as materials which cause poisoning or other difficulties with the skeletal isomerization catalyst, the olefin can be purified by known techniques such as distillation. If diene impurities are present in the olefin, they may be removed by UOP's DEFINE™ process.

Skeletal isomerization of olefin herein can in general be accomplished in any manner known in the art. Suitable constrained skeletal isomerization catalysts are known for various purposes and include those selected from the group consisting of zeolites and silicoaluminophosphates (the latter may simply be termed "aluminophosphates" elsewhere herein) having one-dimensional pore structures with a pore size of from about 4.2 Angstrom to about 7 Angstrom. Preferred examples of such catalysts include: (i) zeolites having ferrierite isotypic framework structure (more preferably H-ferrierites); and (ii) non-zeolite types such as the silicoaluminophosphates including, but not limited to ALPO-31, SAPO-11, SAPO-31 and SAPO-41. Ferrierite types and SAPO-11 or any suitable isotype are especially preferred. The term "isotype" as used herein refers to a catalyst having substantially equivalent framework structure, particularly with respect to pore dimensions. The inventors have discovered that the skeletal isomerization catalysts and process conditions described in U.S. Pat. No. 5,510,306 are especially useful in the instant invention. U.S. Pat. No. 5,510,306 describes an active and stable catalyst for isomerizing linear olefin to methyl branched isoolefins which is provided by (a) mixing (i) a zeolite powder containing at least one zeolite with at least one one-dimensional pore structure having pore size small enough to retard by-product dimerization and coke formation and large enough to permit entry of the linear olefin and allow formation of the methyl branched isoolefin; (ii) an alumina-containing binder; (iii) water; (iv) at least one acid selected from monocarboxylic acids and inorganic acids and (v) at least one polycarboxylic acid; (b) forming pellets of the mixture; and (c) calcining the pellet.

The preferred catalysts comprise substantially only zeolites with the specified pore size in one dimension. In more detail, examples of zeolites, aluminophosphates etc. that can be used for skeletal isomerization of the olefin specified herein are the hydrogen form of ferrierite, AlPO-31, SAPO-11, SAPO-31, SAPO-41, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MeAPSO-11, MeAPSO-31, MeAPSO-41, MeAPSO-46, ELAPO-11, ELAPO-31, ELAPO-41, ELAPSO-11, ELAPSO-31, ELAPSO-41, laumontite, cancrinite, offretite, hydrogen form of stilbite, and the magnesium or calcium form of mordenite and partheite. Many natural zeolites such as ferrierite having an initially reduced pore size can be converted to those forms suitable for olefin skeletal isomerization in the instant invention for example by removing associated alkali metal or alkaline earth metal by ammonium ion exchange and calcination to produce the substantially hydrogen form as taught in U.S. Pat. No. 4,795,623 and U.S. Pat. No. 4,924,027. Note that H-form mordenite is unsuitable for this process step but is useful in the later step of alkylation as taught hereinafter.

Particularly useful for olefin skeletal isomerization herein is the catalyst is prepared in the manner of Example 1 of U.S. Pat. No. 5,082,956. See also WO 95/21225, e.g., Example 1 and the specification thereof.

Alkylation

The invention further includes, after the delinearization, a monoalkylation step of reacting the delinearized olefin with an aromatic hydrocarbon selected from benzene, toluene and mixtures thereof.

Internal Isomer Selectivity and Selection of Alkylation Step

The present processes require an alkylation step having internal isomer selectivity in the range from 0 to 40, preferably from 0 to 20, more preferably still from 0 to 10. The Internal Isomer Selectivity or "IIS" as defined herein is measured for any given alkylation process step by conducting a test alkylation of benzene by 1-dodecene at a molar ratio of 10:1. The alkylation is conducted in the presence of an alkylation catalyst to a conversion of dodecene of at least 90% and formation of monophenyldodecanes of at least 60%. Internal isomer selectivity is then determined as:

$$IIS = 100 * \left( \frac{1 - amount\ of\ terminal\ phenyldodecanes}{amount\ of\ total\ phenyldodecanes} \right)$$

wherein amounts are amounts of the products by weight; the amount of terminal phenyldodecanes is the amount of the sum of 2-phenyldodecane and 3-phenyldodecane and the amount of total phenyldodecanes is the amount of the sum of 2-phenyldodecane and 3-phenyldodecane and 4-phenyldodecane and 5-phenyldodecane and 6-phenyldodecane and wherein said amounts are determined by any known analytical technique for alkylbenzenesulfonates such as gas chromatography. See Analytical Chemistry, Nov. 1983, 55 (13), 2120–2126, Eganhouse et al, "Determination of long-chain alkylbenzenes in environmental samples by argentation thin-layer chromatography—high resolution gas chromatography and gas chromatography/mass spectrometry". In computing IIS according to the above formula, the amounts are divided before subtracting the result from 1 and multiplying by 100. It should of course be understood that the specific alkenes used to characterize or test any given alkylation step for suitability are reference materials permitting a comparison of the alkylation step herein with known alkylation steps as used in making linear alkylbenzenes and permitting the practitioner of the invention to decide if a given known alkylation step is, or is not, useful in the context of the series of process steps constituting the present invention. In the process of the invention as practiced, the hydrocarbon feedstock for alkylation actually used is of course that which is specified on the basis of the preceding process steps. Also to be noted, all the current commercial processes for LAS manufacture are excluded from the present invention solely on the basis of the IIS for the alkylation step. For example, LAS processes based on aluminum chloride, HF and the like all have IIS outside of the range specified for the instant process. In contrast, a few alkylation steps described in the literature but not currently applied in commercial alkylbenzenesulfonate production do have suitable IIS and are useful herein.

The better to assist the practitioner in determining IIS and in deciding whether a given alkylation process step is suitable for the purposes of the present invention, the following are more particular examples of IIS determination.

As noted, test alkylation of benzene by 1-dodecene is conducted at a mole ratio of 10:1 benzene to 1-dodecene and the alkylation is conducted in the presence of an alkylation catalyst to a conversion of dodecene of at least 90% and formation of monophenyldodecanes of at least 60%. The alkylation test must in general be conducted in a reaction time of less than 200 hours and at a reaction temperature of from about −15° C. to about 500° C., preferably from about 20° C. to 500° C. Pressure and catalyst concentration relative to 1-dodecene can vary widely. No solvent other than benzene is used in the test alkylation. The process conditions used to determine the IIS for the catalyst or alkylation step in question can be based on the literature. The practitioner will use generally appropriate conditions based on a large body of well-documented data for alkylations. For example, appropriate process conditions to determine if an AlCl$_3$ alkylation can be used herein are exemplified by a reaction of 5 mole % AlCl$_3$ relative to 1-dodecene at 20–40°

C. for 0.5–1.0 hour in a batch reactor. Such a test demonstrates that an AlCl₃ alkylation step is unsuitable for use in the present process. An IIS of about 48 should be obtained. In another example, an appropriate test of alkylation using HF as a catalyst should give an IIS of about 60. Thus, neither AlCl₃ alkylation nor HF alkylation is within the scope of this invention. For a medium-pore zeolite such as a dealuminized mordenite, process conditions suitable for determining IIS are exemplified by passing 1-dodecene and benzene at a mole ratio of 10:1 across the mordenite catalyst at a WHSV of 30 $Hr^{-1}$ at a reaction temperature of about 200° C. and a pressure of about 200 psig which should give an IIS of about 0 for the mordenite catalyst. The temperatures and pressures for the exemplary mordenite alkylation test (see also the detailed examples of the instant process hereinafter) are expected to be more generally useful for testing zeolites and other shape-selective alkylation catalysts. Using a catalyst such as H-ZSM-4 one should obtain an IIS of about 18. Clearly both the dealuminized mordenite and H-ZSM-4 catalyzed alkylations give acceptable IIS for the invention, with the mordenite being superior.

Alkylation Catalyst

Accomplishing the required IIS in the alkylation process step is made possible by a tightly controlled selection of alkylation catalysts. Numerous alkylation catalysts are readily determined to be unsuitable. Unsuitable alkylation catalysts include the DETAL® process catalysts, aluminum chloride, HF, HF on zeolites, fluoridated zeolites, non-acidic calcium mordenite, and many others. Indeed no alkylation catalyst currently used for alkylation in the commercial production of detergent linear alkylbenzenesulfonates has yet been found suitable.

In contrast, suitable alkylation catalyst herein is selected from shape-selective moderately acidic alkylation catalysts, preferably zeolitic. The zeolite in such catalysts for the alkylation step (step (b)) is preferably selected from the group consisting of mordenite, ZSM-4, ZSM-12, ZSM-20, offretite, gmelinite and zeolite beta in at least partially acidic form. More preferably, the zeolite in step (b) (the alkylation step) is substantially in acid form and is contained in a catalyst pellet comprising a conventional binder and further wherein said catalyst pellet comprises at least about 1%, more preferably at least 5%, more typically from 50% to about 90%, of said zeolite.

More generally, suitable alkylation catalyst is typically at least partially crystalline, more preferably substantially crystalline not including binders or other materials used to form catalyst pellets, aggregates or composites. Moreover the catalyst is typically at least partially acidic. Fully exchanged Ca-form mordenite, for example, is unsuitable whereas H-form mordenite is suitable. This catalyst is useful for the alkylation step identified as step (b) in the claims hereinafter: these correspond to Steps G, H and J in FIGS. 2–4.

The pores characterizing the zeolites useful in the present alkylation process may be substantially circular, such as in cancrinite which has uniform pores of about 6.2 angstroms, or preferably may be somewhat elliptical, such as in mordenite. It should be understood that, in any case, the zeolites used as catalysts in the alkylation step of the present process have a major pore dimension intermediate between that of the large pore zeolites, such as the X and Y zeolites, and the relatively small pore size zeolites ZSM-5 and ZSM-11, and preferably between about 6A and about 7A. Indeed ZSM-5 has been tried and found inoperable in the present invention. The pore size dimensions and crystal structures of certain zeolites are specified in *ATLAS OF ZEOLITE STRUCTURE TYPES* by W. M. Meier and D. H. Olson, published by the Structure Commission of the International Zeolite Association (1978 and more recent editions) and distributed by Polycrystal Book Service, Pittsburgh, Pa.

The zeolites useful in the alkylation step of the instant process generally have at least 10 percent of the cationic sites thereof occupied by ions other than alkali or alkaline-earth metals. Typical but non-limiting replacing ions include ammonium, hydrogen, rare earth, zinc, copper and aluminum. Of this group, particular preference is accorded ammonium, hydrogen, rare earth or combinations thereof. In a preferred embodiment, the zeolites are converted to the predominantly hydrogen form, generally by replacement of the alkali metal or other ion originally present with hydrogen ion precursors, e.g., ammonium ions, which upon calcination yield the hydrogen form. This exchange is conveniently carried out by contact of the zeolite with an ammonium salt solution, e.g., ammonium chloride, utilizing well known ion exchange techniques. In certain preferred embodiments, the extent of replacement is such as to produce a zeolite material in which at least 50 percent of the cationic sites are occupied by hydrogen ions.

The zeolites may be subjected to various chemical treatments, including alumina extraction (dealumination) and combination with one or more metal components, particularly the metals of Groups IIB, III, IV, VI, VII and VIII. It is also contemplated that the zeolites may, in some instances, desirably be subjected to thermal treatment, including steaming or calcination in air, hydrogen or an inert gas, e.g. nitrogen or helium.

A suitable modifying treatment entails steaming of the zeolite by contact with an atmosphere containing from about 5 to about 100% steam at a temperature of from about 250° C. to 1000° C. Steaming may last for a period of between about 0.25 and about 100 hours and may be conducted at pressures ranging from sub-atmospheric to several hundred atmospheres.

In practicing the desired alkylation step of the instant process, it may be useful to incorporate the above-described intermediate pore size crystalline zeolites in another material, e.g., a binder or matrix resistant to the temperature and other conditions employed in the process. Such matrix materials include synthetic or naturally occurring substances as well as inorganic materials such as clay, silica, and/or metal oxides. Matrix materials can be in the form of gels including mixtures of silica and metal oxides. The latter may be either naturally occurring or in the form of gels or gelatinous precipitates. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the intermediate pore size zeolites employed herein may be compounded with a porous matrix material, such as alumina, silica-alumina, silica-magnesia, silica-zirconia, silica-thoria, silica-beryllia, and silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely, with the zeolite content ranging from between about 1 to about 99% by weight and more usually in the range of about 5 to about 80% by weight of the composite.

A group of zeolites which includes some useful for the alkylation step herein have a silica:alumina ratio of at least 10:1, preferably at least 20:1. The silica:alumina ratios referred to in this specification are the structural or framework ratios, that is, the ratio for the $SiO_4$ to the $AlO_4$ tetrahedra. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as the dealuminization methods described below which result in the presence of ionic aluminum free of the zeolite structure are employed. Due care should therefore be taken to ensure that the framework silica:alumina ratio is correctly determined.

Zeolite beta suitable for use herein (but less preferred than H-mordenite) is disclosed in U.S. Pat. No. 3,308,069 to which reference is made for details of this zeolite and its preparation. Such a zeolite in the acid form is also commercially available as Zeocat PB/H from Zeochem.

When the zeolites have been prepared in the presence of organic cations they are catalytically inactive, possibly because the intracrystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of the zeolite; but it does appear to favor the formation of this special type of zeolite. Some natural zeolites may sometimes be converted to zeolites of the desired type by various activation procedures and other treatments such as base exchange, steaming, alumina extraction and calcination. The zeolites preferably have a crystal framework density, in the dry hydrogen form, not substantially below about 1.6 g.cm −3. The dry density for known structures may be calculated from the number of silicon plus aluminum atoms per 1000 cubic Angstroms, as given, e.g., on page 19 of the article on Zeolite Structure by W. M. Meier included in "Proceedings of the Conference on Molecular Sieves, London, April 1967", published by the Society of Chemical Industry, London, 1968. Reference is made to this paper for a discussion of the crystal framework density. A further discussion of crystal framework density, together with values for some typical zeolites, is given in U.S. Pat. No. 4,016,218, to which reference is made. When synthesized in the alkali metal form, the zeolite is conveniently converted to the hydrogen form, generally by intermediate formation of the ammonium form as a result of ammonium ion exchange and calcination of the ammonium form to yield the hydrogen form. It has been found that although the hydrogen form of the zeolite catalyzes the reaction successfully, the zeolite may also be partly in the alkali metal form.

EP 466,558 describes an acidic mordenite type alkylation catalyst also of possible use herein having overall Si/Al atomic ratio of 15–85 (15–60), Na weight content of less than 1000 ppm (preferably less than 250 ppm), having low or zero content of extra-network Al species, and an elementary mesh volume below 2,760 nm3.

U.S. Pat. No. 5,057,472 useful for preparing alkylation catalysts herein relates to concurrent dealumination and ion-exchange of an acid-stable Na ion-containing zeolite, preferably mordenite effected by contact with a 0.5–3 (preferably 1–2.5) M HNO3 solution containing sufficient NH4NO3 to fully exchange the Na ions for NH4 and H ions. The resulting zeolites can have an $SiO_2:Al_2O_3$ ratio of 15–26 (preferably 17–23):1 and are preferably calcined to at least partially convert the $NH_4/H$ form to an H form. Optionally, though not necessarily particularly desirable in the present invention, the catalyst can contain a Group VIII metal (and optionally also an inorganic oxide) together with the calcined zeolite of '472.

Another acidic mordenite catalyst useful for the alkylation step herein is disclosed in U.S. Pat. No. 4,861,935 which relates to a hydrogen form mordenite incorporated with alumina, the composition having a surface area of at least 580 m2/g. Other acidic mordenite catalysts useful for the alkylation step herein include those described in U.S. Pat. No. 5,243,116 and U.S. Pat. No. 5,198,595. Yet another alkylation catalyst useful herein is described in U.S. Pat. No. 5,175,135 which is an acid mordenite zeolite having a silica/alumina molar ratio of at least 50:1, a Symmetry Index of at least 1.0 as determined by X-ray diffraction analysis, and a porosity such that the total pore volume is in the range from about 0.18 cc/g to about 0.45 cc/g and the ratio of the combined meso- and macropore volume to the total pore volume is from about 0.25 to about 0.75.

Particularly preferred alkylation catalysts herein include the acidic mordenite catalysts Zeocatm™FM-8/25H available from Zeochem; CBV 90 A available from Zeolyst International, and LZM-8 available from UOP Chemical Catalysts.

Most generally, any alkylation catalyst may be used herein provided that the alkylation step meets the internal isomer selectivity requirements identified supra.

Process based on Paraffinic Feedstocks

In another aspect, the present invention relates to a process for preparing modified alkylbenzenesulfonate surfactant suitable for use in cleaning products, said process comprising (a) a step of arriving at (making or providing) a reduced-linearity alkylating agent selected from an olefin having molecular weight of at least about 126 and no more than about 280 and produced by a sequence of steps comprising: (i) skeletally isomerizing a linear paraffin having molecular weight of n+2 wherein n is said molecular weight of said olefin; and (ii) dehydrogenating the isomerized paraffin; and (b) a monoalkylation step having an internal isomer selectivity of from 0 to 40 comprising reacting the product of step (a) with an aromatic hydrocarbon selected from benzene, toluene and mixtures thereof in the presence of an alkylation catalyst. The alkylation catalyst is identical with the alkylation catalyst for step (b) in the above-defined processes starting from olefin feedstocks. The product of this process can be sulfonated, neutralized and blended or mixed with cleaning product ingredients as defined for the inventive process based on olefin feedstocks described herein.

Skeletal Isomerization of Linear Paraffin

Preferred starting-material paraffins for delinearization of paraffins by skeletal isomerization herein are linear paraffins having the required molecular weight. Suitable paraffins can more generally be obtained from any source. As used, the paraffins can contain, in addition to linear paraffin, varying amounts of other material, such as isoparaffins or olefins, as long as such materials do not materially interfere with the skeletal isomerization step. If paraffin raw materials contain unacceptable impurities, such as materials which cause poisoning or other difficulties with the skeletal isomerization catalyst, the linear paraffin can be purified by known techniques such as distillation or catalytic hydrogenolysis to remove sulfur-containing impurities. Suitable paraffin feedstocks must contain linear paraffins and such feedstocks are commonly based on kerosene treated by UOP's MOLEX™ process.

In general, any catalyst suitable for alkyl branching, preferably methyl branching, of a linear paraffin is useful in the instant process. Preferred skeletal isomerization catalysts for this step include (i) zeolites having ferrierite isotypic framework structure (more preferably H-ferrierites); (see for example U.S. Pat. No. 5,510,306) and (ii) ALPO-31, SAPO-11, SAPO-31 and SAPO-41.

SAPO-11 containing catalyst systems are preferred and can include both Pt-SAPO-11 and Pd-SAPO-11 though the platinum form is preferred. See U.S. Pat. No. 5,246,566 and S. J. Miller, Microporous Materials, Vol. 2 (1994) 439–449; the latter reference also provides a comparison with several other useful linear paraffin isomerization catalysts which are listed in detail but no such catalyst is as effective as the SAPO-11 containing systems. Despite the apparent irrelevance of a paper on lube oil dewaxing, Miller is insightful in teachings which are herein found applicable to alkylbenzenesulfonate manufacture. For example, at p. 440 of the above-cited Microporous Materials article, Miller teaches low selectivity of SAPO-11 for gem-dimethyl species with preference for methyl branching separated by more than one carbon. Use of SAPO-11 in the paraffin skeletal isomerization step of the instant process is expected to confer exactly such properties to the branched hydrocarbon used in making the modified alkylbenzenes, alkylbenzenesulfonate surfactants and consumer cleaning compositions herein.

Dehydroyenation of Skeletally Isomerized Paraffin

In general, dehydrogenation of the skeletally isomerized paraffin in the instant process can be accomplished using any of the well-known dehydrogenation catalyst systems or "conventional dehydrogenation catalysts" including those described in the Surfactant Science Series references cited in the background as well as in "Detergent Manufacture Including Zeolite Builders and Other New Materials", Ed. Sittig, Noyes Data Corp., New Jersey, 1979 and other dehydrogenation catalyst systems, for example those commercially available though UOP Corp. Dehydrogenation can be conducted in presence of hydrogen gas and commonly a precious metal catalyst is present though alternatively non-hydrogen, precious-metal free dehydrogenation systems such as a zeolite/air system can be used with no precious metals present.

As is well known, dehydrogenation can be complete or partial, more typically partial. When partial, this step forms a mixture of olefin and unreacted paraffin. Such mixture is a suitable feed for the alkylation step of the instant process.

Alkylation in Paraffin-based Process

The alkylation step and alkylation catalysts in paraffin-based processes herein is identical with the alkylation step and alkylation catalysts disclosed in connection with the olefin-based process described in detail hereinabove.

Post-Alkylation Steps

The present invention also encompasses a process according to any of the foregoing aspects or embodiments (whether paraffin-based or olefin-based) having the additional steps, of (c) sulfonating the product of step (b); and one or more steps selected from (d) neutralizing the product of step (c); and (e) mixing the product of step (c) or (d) with one or more cleaning product adjunct materials; thereby forming a cleaning product.

Distillation of Modified Alkylbenzenes

Optionally, depending on feedstock and the precise sequence of steps used, the present process can include distillation of modified alkylbenzenes, for example to remove unreacted starting materials, paraffins, excesses of benzene and the like. Any conventional distillation apparatus can be used. The general practice is similar to that used for distillation of commercial linear alkylbenzenes (LAB). Suitable distillation steps are described in the hereinabove-referenced Surfactant Science Series review of alkylbenzenesulfonate manufacture.

Sulfonation and Workup

In general, sulfonation of the modified alkylbenzenes in the instant process can be accomplished using any of the well-known sulfonation systems, including those described in the hereinabove-referenced volume "Detergent Manufacture Including Zeolite Builders and Other New Materials" as well as in the hereinabove-referenced Surfactant Science Series review of alkylbenzenesulfonate manufacture. Common sulfonation systems include sulfuric acid, chlorosulfonic acid, oleum, sulfur trioxide and the like. Sulfur trioxide/air is especially preferred. Details of sulfonation using a suitable air/sulfur trioxide mixture are provided in U.S. Pat. No. 3,427,342, Chemithon.

Any convenient workup steps may be used in the present process. Common practice is to neutralize after sulfonation with any suitable alkali. Thus the neutralization step can be conducted using alkali selected from sodium, potassium, ammonium, magnesium and substituted ammonium alkalis and mixtures thereof. Potassium can assist solubility, magnesium can promote soft water performance and substituted ammonium can be helpful for formulating specialty variations of the instant surfactants. Sodium-form alkali such as sodium hydroxide is most commonly used. Preferred alkali more generally is selected from sodium hydroxide, potassium hydroxide, ammonium hydroxide, sodium carbonate, potassium carbonate, and mixtures thereof. The invention encompasses any of the derivative forms of the modified alkylbenzenesulfonate surfactants as produced by the present process and their use in consumer product compositions.

Alternately the acid form of the present surfactants can be added directly to acidic cleaning products, or can be mixed with cleaning ingredients and then neutralized.

Blended Embodiments

In one preferred embodiment, prior to the sulfonation step in the instant process, modified alkylbenzene which is the product of said step (c) is blended with a linear alkylbenzene, such as a linear $C_{10}$–$C_{14}$ alkylbenzene, produced by a conventional process. In another such embodiment, in any step subsequent to said sulfonation step, modified alkylbenzene sulfonate (acid-form or neutralized form) produced in accordance with the present process is blended with a linear alkylbenzene sulfonate, such as a linear $C_{10}$–$C_{14}$ alkylbenzene sulfonate (acid-form or neutralized form) produced by a conventional process. In these blended embodiments, blends can be made at a weight ratio of the linear and modified alkylbenzenes or their derivatives of from 100:1 to 1:100. A preferred process has a ratio of modified alkylbenzene to linear alkylbenzene compounds of from about 10:90 to about 50:50. Another preferred process has a ratio of modified alkylbenzene to linear alkylbenzene compounds of from about 51:49 to about 92:8.

Formulation into Cleaning Products

The present invention also encompasses a cleaning product formed by the instant process comprising:
(a) from about 0.1% to about 99.8%, more typically up to about 50%, of modified alkylbenzenesulfonate surfactant as prepared herein and
(b) from about 0.00001%, more typically at least about 1%, to about 99.9% of one or more of said cleaning product adjunct materials.

Adjunct materials can vary widely and accordingly can be used at widely ranging levels. For example, detersive enzymes such as proteases, amylases, cellulases, lipases and the like as well as bleach catalysts including the macrocyclic types having manganese or similar transition metals all useful in laundry and cleaning products can be used herein at very low, or less commonly, higher levels.

Other cleaning product adjunct materials suitable herein include bleaches, especially the oxygen bleach types including activated and catalyzed forms with such bleach activators as nonanoyloxybenzenesulfonate and/or tetraacetylethylenediamine and/or any of its derivatives or derivatives of phthaloylimidoperoxycaproic acid or other imido- or amido-substituted bleach activators including the lactam types, or more generally any mixture of hydrophilic and/or hydrophobic bleach activators (especially acyl derivatives including those of the $C_6$–$C_{16}$ substituted oxybenzenesulfonates); preformed peracids related to or based on any of the hereinbefore mentioned bleach activators, builders including the insoluble types such as zeolites including zeolites A, P and the so-called maximum aluminum P as well as the soluble types such as the phosphates and polyphosphates, any of the hydrous, water-soluble or water-insoluble silicates, 2,2'-oxydisuccinates, tartrate succinates, glycolates, NTA and many other ethercarboxylates or citrates, chelants including EDTA, S,S'-EDDS, DTPA and phosphonates, water-soluble polymers, copolymers and terpolymers, soil release polymers, cosurfactants including any of the known anionic, cationic, nonionic or zwitterionic types, optical brighteners, processing aids such as crisping agents and/fillers, solvents, antiredeposition agents, silicone/silica and other suds suppressors, hydrotropes, perfumes or pro-perfumes, dyes, photobleaches, thickeners, simple salts and alkalis such as those based on sodium or potassium including the hydroxides, carbonates, bicarbonates and sulfates and the like. When combined with the modified alkylbenzenesulfonate surfactants of the instant process, any of the anhydrous, hydrous, water-based or solvent-borne cleaning products are readily accessible as granules, liquids, tablets, powders, flakes, gels, extrudates, pouched or encapsulated forms or the like. Accordingly the present invention also includes the various cleaning products made possible or formed by any of the processes described. These may be used in discrete dosage forms, used by hand or by machine, or may be continuously dosed into all suitable cleaning appliances or delivery devices.

Cleaning Products in Detail

References cited herein are incorporated by reference. The surfactant compositions prepared by the processes of the present invention can be used in a wide range of consumer cleaning product compositions including powders, granules, gels, pastes, tablets, pouches, bars, types delivered in dual-compartment containers, spray or foam detergents and other homogeneous or multiphasic consumer cleaning product forms. They can be used or applied by hand and/or can be applied in unitary or freely alterable dosage, or by automatic dispensing means, or are useful in appliances such as washing-machines or dishwashers or can be used in institutional cleaning contexts, including for example, for personal cleansing in public facilities, for bottle washing, for surgical instrument cleaning or for cleaning electronic components. They can have a wide range of pH, for example from about 2 to about 12 or higher, and they can have a wide range of alkalinity reserve which can include very high alkalinity reserves as in uses such as drain unblocking in which tens of grams of NaOH equivalent can be present per 100 grams of formulation, ranging through the 1–10 grams of NaOH equivalent and the mild or low-alkalinity ranges of liquid hand cleaners, down to the acid side such as in acidic hard-surface cleaners. Both high-foaming and low-foaming detergent types are encompassed.

Consumer product cleaning compositions are described in the "Surfactant Science Series", Marcel Dekker, New York, Volumes 1–67 and higher. Liquid compositions in particular are described in detail in the Volume 67, "Liquid Detergents", Ed. Kuo-Yann Lai, 1997, ISBN 0-8247-9391-9 incorporated herein by reference. More classical formulations, especially granular types, are described in "Detergent Manufacture including Zeolite Builders and Other New Materials", Ed. M. Sittig, Noyes Data Corporation, 1979 incorporated by reference. See also Kirk Othmer's Encyclopedia of Chemical Technology.

Consumer product cleaning compositions herein nonlimitingly include:

Light Duty Liquid Detergents (LDL): these compositions include LDL compositions having surfactancy improving magnesium ions (see for example WO 97/00930 A; GB 2,292,562 A; U.S. Pat. No. 5,376,310; U.S. Pat. No. 5,269, 974; U.S. Pat. No. 5,230,823; U.S. Pat. No. 4,923,635; U.S. Pat. No. 4,681,704; U.S. Pat. No. 4,316,824; U.S. Pat. No. 4,133,779) and/or organic diamines and/or various foam stabilizers and/or foam boosters such as amine oxides (see for example U.S. Pat. No. 4,133,779) and/or skin feel modifiers of surfactant, emollient and/or enzymatic types including proteases; and/or antimicrobial agents; more comprehensive patent listings are given in Surfactant Science Series, Vol. 67, pages 240–248.

Heavy Duty Liquid Detergents (HDL): these compositions include both the so-called "structured" or multi-phase (see for example U.S. Pat. No. 4,452,717; U.S. Pat. No. 4,526,709; U.S. Pat. No. 4,530,780; U.S. Pat. No. 4,618,446; U.S. Pat. No. 4,793,943; U.S. Pat. No. 4,659,497; U.S. Pat. No. 4,871,467; U.S. Pat. No. 4,891,147; U.S. Pat. No. 5,006,273; U.S. Pat. No. 5,021,195; U.S. Pat. No. 5,147,576; U.S. Pat. No. 5,160,655) and "non-structured" or isotropic liquid types and can in general be aqueous or nonaqueous (see, for example EP 738,778 A; WO 97/00937 A; WO 97/00936 A; EP 752,466 A; DE 19623623 A; WO 96/10073 A; WO 96/10072 A; U.S. Pat. No. 4,647,393; U.S. Pat. No. 4,648,983; U.S. Pat. No. 4,655,954; U.S. Pat. No. 4,661,280; EP 225,654; U.S. Pat. No. 4,690,771; U.S. Pat. No. 4,744, 916; U.S. Pat. No. 4,753,750; U.S. Pat. No. 4,950,424; U.S. Pat. No. 5,004,556; U.S. Pat. No. 5,102,574; WO 94/23009; and can be with bleach (see for example U.S. Pat. No. 4,470,919; U.S. Pat. No. 5,250,212; EP 564,250; U.S. Pat. No. 5,264,143; U.S. Pat. No. 5,275,753; U.S. Pat. No. 5,288,746; WO 94/11483; EP 598,170; EP 598,973; EP 619,368; U.S. Pat. No. 5,431,848; U.S. Pat. No. 5,445,756) and/or enzymes (see for example U.S. Pat. No. 3,944,470; U.S. Pat. No. 4,111,855; U.S. Pat. No. 4,261,868; U.S. Pat. No. 4,287,082; U.S. Pat. No. 4,305,837; U.S. Pat. No. 4,404,115; U.S. Pat. No. 4,462,922; U.S. Pat. No. 4,529, 5225; U.S. Pat. No. 4,537,706; U.S. Pat. No. 4,537,707; U.S. Pat. No. 4,670,179; U.S. Pat. No. 4,842,758; U.S. Pat. No. 4,900,475; U.S. Pat. No. 4,908,150; U.S. Pat. No. 5,082,585; U.S. Pat. No. 5,156,773; WO 92/19709; EP 583,534; EP 583,535; EP 583,536; WO 94/04542; U.S. Pat. No. 5,269, 960; EP 633,311; U.S. Pat. No. 5,422,030; U.S. Pat. No. 5,431,842; U.S. Pat. No. 5,442,100) or without bleach and/or enzymes. Other patents relating to heavy-duty liquid detergents are tabulated or listed in Surfactant Science Series, Vol. 67, pages 309–324.

Heavy Duty Granular Detergents (HDG): these compositions include both the so-called "compact" or agglomerated or otherwise non-spray-dried, as well as the so-called "fluffy" or spray-dried types. Included are both phosphated and nonphosphated types. Such detergents can include the more common anionic-surfactant based types or can be the so-called "high-nonionic surfactant" types in which commonly the nonionic surfactant is held in or on an absorbent such as zeolites or other porous inorganic salts. Manufacture of HDG's is, for example, disclosed in EP 753,571 A; WO 96/38531 A; U.S. Pat. No. 5,576,285; U.S. Pat. No. 5,573,697; WO 96/34082 A; U.S. Pat. No. 5,569,645; EP 739,977 A; U.S. Pat. No. 5,565,422; EP 737,739 A; WO 96/27655 A; U.S. Pat. No. 5,554,587; WO 96/25482 A; WO 96/23048 A; WO 96/22352 A; EP 709,449 A; WO 96/09370 A; U.S. Pat. No. 5,496,487; U.S. Pat. No. 5,489,392 and EP 694,608 A.

"Softerpents" (STW): these compositions include the various granular or liquid (see for example EP 753,569 A; U.S. Pat. No. 4,140,641; U.S. Pat. No. 4,639,321; U.S. Pat. No. 4,751,008; EP 315,126; U.S. Pat. No. 4,844,821; U.S. Pat. No. 4,844,824; U.S. Pat. No. 4,873,001; U.S. Pat. No. 4,911,852; U.S. Pat. No. 5,017,296; EP 422,787) softening-through-the wash types of product and in general can have organic (e.g., quaternary) or inorganic (e.g., clay) softeners.

Hard Surface Cleaners (HSC): these compositions include all-purpose cleaners such as cream cleansers and liquid all-purpose cleaners; spray all-purpose cleaners including glass and tile cleaners and bleach spray cleaners; and bathroom cleaners including mildew-removing, bleach-containing, antimicrobial, acidic, neutral and basic types. See, for example EP 743,280 A; EP 743,279 A. Acidic cleaners include those of WO 96/34938 A.

Bar Soaps and/or Laundry Bars (BS&HW): these compositions include personal cleansing bars as well as so-called laundry bars (see, for example WO 96/35772 A); including both the syndet and soap-based types and types with softener (see U.S. Pat. No. 5,500,137 or WO 96/01889 A); such compositions can include those made by common soap-making techniques such as plodding and/or more unconventional techniques such as casting, absorption of surfactant into a porous support, or the like. Other bar soaps (see for example BR 9502668; WO 96/04361 A; WO 96/04360 A; U.S. Pat. No. 5,540,852) are also included. Other handwash detergents include those such as are described in GB 2,292, 155 A and WO 96/01306 A.

Shampoos and Conditioners (S&C): (see, for example WO 96/37594 A; WO 96/17917 A; WO 96/17590 A; WO 96/17591 A). Such compositions in general include both simple shampoos and the so-called "two-in-one" or "with conditioner" types.

Liquid Soaps (LS): these compositions include both the so-called "antibacterial" and conventional types, as well as those with or without skin conditioners and include types suitable for use in pump dispensers, and by other means such as wall-held devices used institutionally.

Special Purpose Cleaners (SPC): including home dry cleaning systems (see for example WO 96/30583 A; WO 96/30472 A; WO 96/30471 A; U.S. Pat. No. 5,547,476; WO 96/37652 A); bleach pretreatment products for laundry (see EP 751,210 A); fabric care pretreatment products (see for example EP 752,469 A); liquid fine fabric detergent types, especially the high-foaming variety; rinse-aids for dishwashing; liquid bleaches including both chlorine type and oxygen bleach type, and disinfecting agents, mouthwashes, denture cleaners (see, for example WO 96/19563 A; WO 96/19562 A), car or carpet cleaners or shampoos (see, for example EP 751,213 A; WO 96/15308 A), hair rinses, shower gels, foam baths and personal care cleaners (see, for example WO 96/37595 A; WO 96/37592 A; WO 96/37591 A; WO 96/37589 A; WO 96/37588 A; GB 2,297,975 A; GB 2,297,762 A; GB 2,297,761 A; WO 96/17916 A; WO 96/12468 A) and metal cleaners; as well as cleaning auxiliaries such as bleach additives and "stain-stick" or other pre-treat types including special foam type cleaners (see, for example EP 753,560 A; EP 753,559 A; EP 753,558 A; EP 753,557 A; EP 753,556 A) and anti-sunfade treatments (see WO 96/03486 A; WO 96/03481 A; WO 96/03369 A) are also encompassed. Detergents with enduring perfume (see for example U.S. Pat. No. 5,500,154; WO 96/02490) are increasingly popular.

Process Integration

The present process can be integrated with current LAB manufacturing processes in any convenient manner. For example, a conventional erected plant can be switched to produce the modified alkylbenzenes in their entirety. Alternately, depending on volumes desired or feedstocks available, for example as effluents from the LAB process or based on proximity of feedstock sources from the petrochemical industry, plant for the manufacture of the instant modified alkylbenzenes may be erected as an add-on or complement to an existing LAB facility, or as a stand-alone. Both batch and continuous operation of the present process are envisaged.

The present invention should not be considered limited by the specifics of its illustration in the specification including the examples given for illustration hereinafter. Most generally, the present invention should be taken to encompass any consumer cleaning composition comprising any surfactant product of any type wherein the hydrophobe of the surfactant has been modified by an approach using the essential teachings of the instant process. The present teachings, especially with respect to the delinearization approach, are believed to be reapplicable, for example, to the manufacture of modified alkyl sulfates and other surfactants.

Other Embodiments

The present invention is not limited to the specific embodiments thusfar described. Thus, there is encompassed herein a method for improving the cleaning performance of a consumer cleaning product containing alkylarylsulfonate surfactant, said method comprising (a) at least one stage (a stage being one or more steps) of delinearizing a ($C_{10}$–$C_{16}$ alkyl)arene (the arene being benzene or less preferably toluene, xylene, naphthalene or mixtures thereof) to at least a minimum extent of about 0.1 methyl moieties per molecule of said alkylarene and a maximum extent of from about 1 to about 2.5 methyl moieties per molecule of said alkylarene, said stage comprising at least one linearity reduction step conducted prior to, in parallel with, or subsequent to, a step of coupling alkyl precursor and aryl precursor portions of said alkylarene; (these precursors being illustrated by the olefins and/or paraffins described as starting-materials for the processed described hereinabove); (b) at least one step of sulfonating the lightly branched alkylarene product of stage (a); and (c) at least one step of formulating the lightly branched alkylarylsulfonate surfactant product of step (b) in acid or salt form into a cleaning composition.

Such a method includes more particularly the method wherein stage (a) forms 1-phenyl isomers of said alkylarene; the method wherein stage (a) forms 2-phenyl isomers of said alkylarene to an advantageous extent, for example of at least about 60%; the method wherein stage (a) forms at least two homologs of said alkylarenes wherein said alkyl moieties bonded to said aryl moieties contain from 10 to 16 carbon atoms, more preferably from 11 to 14 carbon atoms in total and wherein each of said homologs (any two "homologs" having the same structure excluding isomers but differing by having a different carbon number in the stated range of total carbon atoms) comprises at least two positional isomers with respect to the attachment of said methyl moieties to the balance of the alkyl moieties in said alkylarenes.

Also included are the method wherein stage (a) is conducted without reliance on F-containing or aluminum chloride catalysts; the method wherein stage (a) is conducted without reliance on conventional strongly acid-catalyzed polymerization of propylene, such as HF- or Aluminum Chloride catalyzed polymerization; the method wherein more than 20% of the alkylarene molecules produced in stage (a) have one methyl moiety; the method wherein not more than about 20% of the alkylarene product of stage (a) has two or more methyl moieties; the method wherein stage (a) includes a skeletal rearrangement step conducted after formation of said alkylarene; the method wherein stage (a) includes an isomerization step conducted in parallel with formation of said alkylarene; the method wherein stage (a) comprises Fischer-Tropsch chemistry and/or uses Synthol olefins; the method wherein stage (a) is independent of Fischer-Tropsch chemistry and/or is unreliant on Synthol olefins; the method wherein stage (a) includes use of a fluoride-free dealuminized mordenite catalyst; the method wherein stage (a) includes use of a ferrierite catalyst; and the method wherein stage (a) produces a distribution of molecular weights consistent with presence in said alkylarylene of alkylarylene molecules having a total of carbon atoms including both odd and even carbon totals. Very preferably, any of said methods rely on an alkylation step having internal isomer selectivity in the range of from 0 to 40, more preferably from 0 to 20 or lower.

Moreover there is included herein any cleaning composition comprising an improved surfactant composition produced by any of said methods.

EXAMPLE 1

Modified Alkylbenzenesulfonate Surfactant
Prepared via Skeletally Isomerized Linear Olefin Step (a): At Least Partially Reducing the Linearity of an Olefin (by Skeletal Isomerization of Olefin Preformed to Chainlengths Suitable for Cleaning Product Detergency)

A mixture of 1-decene, 1-undecene, 1-dodecene and 1-tridecene (for example available from Chevron) at a weight ratio of 1:2:2:1 is passed over a Pt-SAPO catalyst at 220° C. and any suitable LHSV, for example 1.0. The catalyst is prepared in the manner of Example 1 of U.S. Pat. No. 5,082,956. See WO 95/21225, e.g., Example 1 and the specification thereof. The product is a skeletally isomerized lightly branched olefin having a range of chainlengths suitable for making alkylbenezenesulfonate surfactant for consumer cleaning composition incorporation. More generally the temperature in this step can be from about 200° C. to about 400° C., preferably from about 230° C. to about 320° C. The pressure is typically from about 15 psig to about 2000 psig, preferably from about 15 psig to about 1000 psig, more preferably from about 15 psig to about 600 psig. Hydrogen is a useful pressurizing gas. The space velocity (LHSV or WHSV) is suitably from about 0.05 to about 20. Low pressure and low hourly space velocity provide improved selectivity, more isomerization and less cracking. Distill to remove any volatiles boiling at up to 40° C./10 mmHg.

Step (b): Alkylating the Product of Step (a) Using an Aromatic Hydrocarbon

To a glass autoclave liner is added 1 mole equivalent of the lightly branched olefin mixture produced in step (a), 20 mole equivalents of benzene and 20 wt. % based on the olefin mixture of a shape selective zeolite catalyst (acidic mordenite catalyst Zeoca™ FM-8/25H). The glass liner is sealed inside a stainless steel rocking autoclave. The autoclave is purged twice with 250 psig $N_2$, and then charged to 1000 psig $N_2$. With mixing, the mixture is heated to 170–190° C. for 14–15 hours at which time it is then cooled and removed from the autoclave. The reaction mixture is filtered to remove catalyst and is concentrated by distilling off unreacted starting-materials and/or impurities (e.g., benzene, olefin, paraffin, trace materials, with useful materials being recycled if desired) to obtain a clear near-colorless liquid product. The product formed is a desirable modified alkylbenzene mixture which can, as an option, be shipped to a remote manufacturing facility where the additional steps of sulfonation and incorporation into consumer cleaning compositions can be accomplished.

Step (c): Sulfonating the Product of Step (b)

The modified alkylbenzene mixture of step (b) is sulfonated with an equivalent of chlorosulfonic acid using methylene chloride as solvent. The methylene chloride is distilled away.

Step (d): Neutralizing the Product of Step (c)

The product of step (c) is neutralized with sodium methoxide in methanol and the methanol evaporated to give modified alkylbenzene sulfonate, sodium salt mixture.

EXAMPLE 2

Modified Alkylbenzenesulfonate Surfactant
Prepared via Skeletally Isomerized Linear Olefin The procedure of Example 1 is repeated with the exception that the sulfonating step, (c), uses sulfur trioxide (without methylene chloride solvent) as sulfonating agent. Details of sulfonation using a suitable air/sulfur trioxide mixture are provided in U.S. Pat. No. 3,427,342, Chemithon. Moreover, step (d) uses sodium hydroxide in place of sodium methoxide for neutralization.

EXAMPLE 3

Modified Alkylbenzenesulfonate Surfactant
Prepared via Skeletally Isomerized Linear Olefin Step (a): At Least Partially Reducing the Linearity of an Olefin A lightly branched olefin mixture is prepared by passing a mixture of C11, C12 and C13 mono olefins in the weight ratio of 1:3:1 over H-ferrierite catalyst at 430° C. The method and catalyst of U.S. Pat. No. 5,510,306 can be used for this step. Distill to remove any volatiles boiling at up to 40° C./10 mmHg.

Step (b): Alkylating the Product of Step (a) Using an Aromatic Hydrocarbon

To a glass autoclave liner is added 1 mole equivalent of the lightly branched olefin mixture of step (a), 20 mole equivalents of benzene and 20 wt. % ,based on the olefin mixture, of a shape selective zeolite catalyst (acidic mordenite catalyst Zeoca™ FM-8/25H). The glass liner is sealed inside a stainless steel, rocking autoclave. The autoclave is purged twice with 250 psig $N_2$, and then charged to 1000 psig $N_2$. With mixing, the mixture is heated to 170–190° C. overnight for 14–15 hours at which time it is then cooled and removed from the autoclave. The reaction mixture is filtered to remove catalyst. Benzene is distilled and recycled, volatile impurities also being removed. A clear colorless or nearly colorless liquid product is obtained.

Step (c): Sulfonating the Product of Step (b)

The modified alkylbenzene mixture of step (b) is sulfonated with an equivalent of chlorosulfonic acid using methylene chloride as solvent. The methylene chloride is distilled away.

Step (d): Neutralizing the Product of Step (c)

The product of step (c) is neutralized with sodium methoxide in methanol and the methanol evaporated to give modified alkylbenzene sulfonate, sodium salt mixture.

EXAMPLE 4

Modified Alkylbenzenesulfonate Surfactant
Prepared via Skeletally Isomerized Linear Olefin The procedure of Example 3 is repeated with the exception that the sulfonating step, (c), uses sulfur trioxide (without methylene chloride solvent) as sulfonating agent. Details of sulfonation using a suitable air/sulfur trioxide mixture are provided in U.S. Pat. No. 3,427,342, Chemithon.

EXAMPLE 5

Cleaning Composition

The procedure of Example 1 is repeated with the exception that the product of step (d) is further treated by the following additional step, (e).

Step (e): Incorporation of the Product of Step (d) into a Cleaning Composition 10% by weight of the product of step (d) is combined with 90% by weight of an agglomerated compact laundry detergent granule.

EXAMPLE 6

Modified Alkylbenzenesulfonate Surfactant
Prepared via Skeletally Isomerized Linear Olefin In Example 1, step (b) is replaced by the following:
Step (b): Alkylating the Product of Step (a) using an Aromatic Hydrocarbon To a glass autoclave liner is added 1 mole equivalent of the lightly branched olefin mixture of step (a), 20 mole equivalents of benzene and 20 wt. %, based on the olefin mixture, of a shape selective zeolite catalyst (acidic zeolite beta ZEOCAT™ PB/H). The glass liner is sealed inside a stainless steel, rocking autoclave. The autoclave is purged twice with 250 psig $N_2$, and then charged to 1000 psig $N_2$. With mixing, the mixture is heated to 145–150° C. overnight for 14–15 hours at which time it is then cooled and removed from the autoclave. The reaction mixture is filtered to remove catalyst. Benzene is distilled and recycled, volatile impurities also being removed. A clear colorless or nearly colorless liquid product is obtained.

EXAMPLE 7

Modified Alkylbenzenesulfonate Surfactant
Prepared via Skeletally Isomerized Linear Olefin The procedure of Example 6 is followed except that the shape selective zeolite catalyst in step (b) is replaced with HZSM-12 as described in U.S. Pat. No. 3,832,449 and the reaction temperature for step (b) is about 200–220° C.

EXAMPLE 8

Modified Alkylbenzenesulfonate Surfactant
Prepared via Skeletally Isomerized Linear Olefin The procedure of Example 1 is followed except that in step (b), the molar ratio of benzene to olefin mixture is 5:1.

EXAMPLE 9

Modified Alkylbenzenesulfonate Surfactant
Prepared via Skeletally Isomerized Linear Olefin The procedure of Example 1 is repeated, except that the neutralizing agent in step (d) is sodium hydroxide instead of sodium methoxide.

EXAMPLE 10

Modified Alkylbenzenesulfonate Surfactant
Prepared via Skeletally Isomerized Linear Olefin The procedure of Example 1 is repeated, except that the sulfonating agent in step (c) is oleum and the neutralizing agent in step (d) is potassium hydroxide instead of sodium methoxide.

EXAMPLE 11

Modified Alkylbenzenesulfonate Surfactant
Prepared via Skeletal Isomerization of Paraffin Step (a i)

A mixture of n-undecane, n-dodecane, n-tridecane, 1:3:1 wt., is isomerized over Pt-SAPO-11 for a conversion better than 90% at a temperature of about 300–340° C., at 1000 psig under hydrogen gas, with a weight hourly space velocity in the range 2–3 and 30 moles H2/mole hydrocarbon. More detail of such an isomerization is given by S. J. Miller in Microporous Materials, Vol. 2, (1994), 439–449. In further examples the linear starting paraffin mixture can be the same as used in conventional LAB manufacture. Distill to remove any volatiles boiling at up to 40° C./10 mmHg.

Step (a ii)

The paraffin of step (a i) can be dehydrogenated using conventional methods. See, for example, U.S. Pat. No. 5,012,021, Apr. 30, 1991 or U.S. Pat. No. 3,562,797, Feb. 9, 1971. Suitable dehydrogenation catalyst is any of the catalysts disclosed in U.S. Pat. No. 3,274,287; U.S. Pat. No. 3,315,007; U.S. Pat. No. 3,315,008; U.S. Pat. No. 3,745,112; U.S. Pat. No. 4,430,517; and U.S. Pat. No. 3,562,797. For purposes of the present example, dehydrogenation is in accordance with U.S. Pat. No. 3,562,797. The catalyst is zeolite A. The dehydrogenation is conducted in the vapor phase in presence of oxygen (paraffin:dioxygen 1:1 molar). The temperature is in range 450° C.–550° C. Ratio of grams of catalyst to moles of total feed per hour is 3.9.

Step (b): Alkylating the Product of Step (a) Using an Aromatic Hydrocarbon

To a glass autoclave liner is added 1 mole equivalent of the mixture of step (a), 5 mole equivalents of benzene and 20 wt. %, based on the olefin mixture, of a shape selective zeolite catalyst (acidic mordenite catalyst Zeocat™ FM-8/25H). The glass liner is sealed inside a stainless steel, rocking autoclave. The autoclave is purged twice with 250 psig $N_2$, and then charged to 1000 psig $N_2$. With mixing, the mixture is heated to 170–190° C. overnight for 14–15 hours at which time it is then cooled and removed from the autoclave. The reaction mixture is filtered to remove catalyst. Benzene and any unreacted paraffins are distilled and recycled. A clear colorless or nearly colorless liquid product is obtained.

Step (c): Sulfonating the Product of Step (b)

The modified alkylbenzene mixture of step (b) is sulfonated with sulfur trioxide/air using no solvent. See U.S. Pat. No. 3,427,342. The molar ratio of sulfur trioxide to alkylbenzene is from about 1.05:1 to about 1.15:1. The reaction stream is cooled and separated from excess sulfur trioxide.

Step (d): Neutralizing the Product of Step (c)

The product of step (c) is neutralized with a slight excess of sodium hydroxide to give modified alkylbenzene sulfonate, sodium salt.

EXAMPLE 12

The process of Example 1 is repeated using different aromatic hydrocarbons. In one run, toluene replaces benzene. In a second run, a mixture of toluene (2%) and benzene (98%) is used.

EXAMPLE 13

Cleaning Product Compositions

In this Example, the following abbreviation is used for a modified alkylbenzene sulfonate, sodium salt form or potassium salt form, prepared according to any of the preceding process examples: MAS The following abbreviations are used for cleaning product adjunct materials:

|  |  |
|---|---|
| APA | Amylolytic enzyme, 60 KNU/g, NOVO, Termamyl ® 60T<br>C8–C10 amido propyl dimethyl amine |
| Bicarbonate | Sodium bicarbonate, anhydrous, 400 μm–1200 μm |
| Borax | Na tetraborate decahydrate |
| Brightener 1 | Disodium 4,4'-bis(2-sulphostyryl)biphenyl |
| Brightener 2 | Disodium 4,4'-bis(4-anilino-6-morpholino-1.3.5-triazin-2-yl)amino) stilbene-2:2'-disulfonate |
| C45AS | C14–C15 linear alkyl sulfate, Na salt |
| CaCl2 | Calcium chloride |
| Carbonate | $Na_2CO_3$ anhydrous, 200 μm–900 μm |
| Cellulase | Cellulolytic enzyme, 1000 CEVU/g, NOVO, Carezyme ® |
| Citrate | Trisodium citrate dihydrate, 86.4%, 425 μm–850 μm |
| Citric Acid | Citric Acid, Anhydrous |
| CMC | Sodium carboxymethyl cellulose |
| CxyAS | $C_{1x}$–$C_{1y}$ alkyl sulfate, Na salt or other salt if specified |
| CxyEz | $C_{1x-1y}$ branched primary alcohol ethoxylate (average z moles of ethylene oxide) |
| CxyEzS | $C_{1x}$–$C_{1y}$ alkyl ethoxylate sulfate, Na salt (average z moles of ethylene oxide; other salt if specified) |
| CxyFA | $C_{1x}$–$C_{1y}$ fatty acid |
| Diamine | Alkyl diamine, e.g., 1,3 propanediamine, Dytek EP, Dytek A, (Dupont) |
| Dimethicone | 40 (gum)/60 (fluid) wt. blend of SE-76 dimethicone gum (G.E Silicones Div.)/dimethicone fluid of viscosity 350 cS. |
| DTPA | Diethylene triamine pentaacetic acid |
| DTPMP | Diethylene triamine penta (methylene phosphonate), Monsanto (Dequest 2060) |
| Endolase | Endoglucanase, activity 3000 CEVU/g, NOVO |
| EtOH | Ethanol |
| Fatty Acid (C12/14) | C12–C14 fatty acid |
| Fatty Acid (RPS) | Rapeseed fatty acid |
| Fatty Acid (TPK) | Topped palm kernel fatty acid |
| HEDP | 1,1-hydroxyethane diphosphonic acid |
| Isofol 16 | C16 (average) Guerbet alcohols (Condea) |
| LAS | Linear Alkylbenzene Sulfonate (C11.8, Na or K salt) |
| Lipase | Lipolytic enzyme, 100 kLU/g, NOVO, Lipolase ® |
| LMFAA | C12–14 alkyl N-methyl glucamide |
| LMFAA | C12–14 alkyl N-methyl glucamide |
| MA/AA | Copolymer 1:4 maleic/acrylic acid, Na salt, avg. mw. 70,000. |
| $MBAE_x$ | Mid-chain branched primary alkyl ethoxylate (average total carbons = x; average EO = 8) |
| $MBAE_xS_z$ | Mid-chain branched primary alkyl ethoxylate sulfate, Na salt (average total carbons = z; average EO = x) |
| $MBAS_x$ | Mid-chain branched primary alkyl sulfate, Na salt (average total carbons = x) |
| MEA | Monoethanolamine |
| MES | Alkyl methyl ester sulfonate, Na salt |
| $MgCl_2$ | Magnesium chloride |
| MnCAT | Macrocyclic Manganese Bleach Catalyst as in EP 544,440 A or, preferably, use [Mn(Bcyclam)$Cl_2$] wherein Bcyclam = 5,12-dimethyl-1,5,8,12-tetraaza-bicyclo[6.6.2]hexadecane or a comparable bridged tetra-aza macrocycle |
| NaDCC | Sodium dichloroisocyanurate |
| NaOH | Sodium hydroxide |
| NaPS | Paraffin sulfonate, Na salt |
| NaSKS-6 | Crystalline layered silicate of formula δ-$Na_2Si_2O_5$ |
| NaTS | Sodium toluene sulfonate |
| NOBS | Nonanoyloxybenzene sulfonate, sodium salt |
| LOBS | C12 oxybenzenesulfonate, sodium salt |
| PAA | Polyacrylic Acid (mw = 4500) |
| PAE | Ethoxylated tetraethylene pentamine |
| PAEC | Methyl quaternized ethoxylated dihexylene triamine |
| PB1 | Anhydrous sodium perborate bleach of nominal formula $NaBO_2.H_2O_2$ |
| PEG | Polyethylene glycol (mw = 4600) |
| Percarbonate | Sodium Percarbonate, nominal formula $2Na_2CO_3.3H_2O_2$ |
| PG | Propanediol |
| Photobleach | Sulfonated Zinc Phthalocyanine encapsulated in dextrin soluble polymer |
| PIE | Ethoxylated polyethyleneimine |
| Protease | Proteolytic enzyme, 4KNPU/g, NOVO, Savinase ® |
| QAS | $R_2.N^+(CH_3)_x((C_2H_4O)yH)z$ with $R_2 = C_8$–$C_{18}$ x + z = 3, x = 0 to 3, z = 0 to 3, y = 1 to 15. |
| SAS | Secondary alkyl sulfate, Na salt |
| Silicate | Sodium Silicate, amorphous ($SiO_2:Na_2O$; 2.0 ratio) |
| Silicone antifoam | Polydimethylsiloxane foam controller + siloxane-oxyalkylene copolymer as dispersing agent; ratio of foam controller:dispersing agent = 10:1 to 100:1. |
| SRP 1 | Sulfobenzoyl end capped esters with oxyethylene oxy and terephthaloyl backbone |
| SRP 2 | Sulfonated ethoxylated terephthalate polymer |
| SRP 3 | Methyl capped ethoxylated terephthalate polymer |
| STPP | Sodium tripolyphosphate, anhydrous |
| Sulfate | Sodium sulfate, anhydrous |
| TAED | Tetraacetylethylenediamine |
| TFA | C16–18 alkyl N-methyl glucamide |
| Zeolite A | Hydrated Sodium Aluminosilicate, $Na_{12}(AlO_2SiO_2)_{12}.27H_2O$; 0.1–10 μm |
| Zeolite MAP | Zeolite (Maximum aluminum P) detergent grade (Crosfield) |

The example is illustrative of the present invention, but is not meant to limit or otherwise define its scope. All parts, percentages and ratios used are expressed as percent weight unless otherwise noted. The following laundry detergent compositions A to E are prepared in accordance with the invention:

|  | A | B | C | D | E |
|---|---|---|---|---|---|
| MAS | 22 | 16.5 | 11 | 1–5.5 | 10–25 |
| Any Combination of: | 0 | 1–5.5 | 11 | 16.5 | 0–5 |
| C45 AS |  |  |  |  |  |
| C45E1S |  |  |  |  |  |
| LAS |  |  |  |  |  |
| C16 SAS |  |  |  |  |  |
| C14–17 NaPS |  |  |  |  |  |
| C14–18 MES |  |  |  |  |  |
| MBAS16.5 |  |  |  |  |  |
| MBAB2S15.5 |  |  |  |  |  |
| QAS | 0–2 | 0–2 | 0–2 | 0–2 | 0–4 |
| C23E6.5 or C45E7 | 1.5 | 1.5 | 1.5 | 1.5 | 0–4 |
| Zeolite A | 27.8 | 0 | 27.8 | 27.8 | 20–30 |
| Zeolite MAP | 0 | 27.8 | 0 | 0 | 0 |
| PAA | 2.3 | 2.3 | 2.3 | 2.3 | 0–5 |
| Carbonate | 27.3 | 27.3 | 27.3 | 27.3 | 20–30 |
| Silicate | 0.6 | 0.6 | 0.6 | 0.6 | 0–2 |
| PB1 | 1.0 | 1.0 | 0–10 | 0–10 | 0–10 |
| NOBS | 0–1 | 0–1 | 0–1 | 0.1 | 0.5–3 |
| LOBS | 0 | 0 | 0–3 | 0 | 0 |
| TAED | 0 | 0 | 0 | 2 | 0 |
| MnCAT | 0 | 0 | 0 | 0 | 2 ppm |
| Protease | 0–0.5 | 0–0.5 | 0–0.5 | 0–0.5 | 0–0.5 |
| Cellulase | 0–0.3 | 0–0.3 | 0–0.3 | 0–0.3 | 0–0.5 |
| Amylase | 0–0.5 | 0–0.5 | 0–0.5 | 0–0.5 | 0–1 |
| SRP 1 or SRP 2 | 0.4 | 0.4 | 0.4 | 0.4 | 0–1 |
| Brightener 1 or 2 | 0.2 | 0.2 | 0.2 | 0.2 | 0–0.3 |
| PEG | 1.6 | 1.6 | 1.6 | 1.6 | 0–2 |
| Silicone Antifoam | 0.42 | 0.42 | 0.42 | 0.42 | 0–0.5 |
| Sulfate, Moisture & Minors |  |  | Balance |  |  |
| Density (g/L) | 663 | 663 | 663 | 663 | 600–700 |

EXAMPLE 14

Cleaning Product Compositions

The following liquid laundry detergent compositions F to J are prepared in accord with the invention. Abbreviations are as used in the preceding Examples.

|  | F | G | H | I | J |
|---|---|---|---|---|---|
| MAS | 1–7 | 7–12 | 12–17 | 17–22 | 1–35 |
| Any combination of: | 15–21 | 10–15 | 5–10 | 0–5 | 0–25 |
| C25 AExS*Na (x = 1.8–2.5) | | | | | |
| MBAE1.8S15.5 | | | | | |
| MBAS15.5 | | | | | |
| C25 AS (linear to high 2-alkyl) | | | | | |
| C14–17 NaPS | | | | | |
| C12–16 SAS | | | | | |
| C18 1,4 disulfate | | | | | |
| LAS | | | | | |
| C12–16 MES | | | | | |
| LMFAA | 0–3.5 | 0–3.5 | 0–3.5 | 0–3.5 | 0–8 |
| C23E9 or C23E6.5 | 0–2 | 0–2 | 0–2 | 0–2 | 0–8 |
| APA | 0–0.5 | 0–0.5 | 0–0.5 | 0–0.5 | 0–2 |
| Citric Acid | 5 | 5 | 5 | 5 | 0–8 |
| Fatty Acid (TPK or C12/14) | 2 | 2 | 2 | 2 | 0–14 |
| EtOH | 4 | 4 | 4 | 4 | 0–8 |
| PG | 6 | 6 | 6 | 6 | 0–10 |
| MEA | 1 | 1 | 1 | 1 | 0–3 |
| NaOH | 3 | 3 | 3 | 3 | 0–7 |
| Na TS | 2.3 | 2.3 | 2.3 | 2.3 | 0–4 |
| Na formate | 0.1 | 0.1 | 0.1 | 0.1 | 0–1 |
| Borax | 2.5 | 2.5 | 2.5 | 2.5 | 0–5 |
| Protease | 0.9 | 0.9 | 0.9 | 0.9 | 0–1.3 |
| Lipase | 0.06 | 0.06 | 0.06 | 0.06 | 0–0.3 |
| Amylase | 0.15 | 0.15 | 0.15 | 0.15 | 0–0.4 |
| Cellulase | 0.05 | 0.05 | 0.05 | 0.05 | 0–0.2 |
| PAE | 0–0.6 | 0–0.6 | 0–0.6 | 0–0.6 | 0–2.5 |
| PIE | 1.2 | 1.2 | 1.2 | 1.2 | 0–2.5 |
| PAEC | 0–0.4 | 0–0.4 | 0–0.4 | 0–0.4 | 0–2 |
| SRP 2 | 0.2 | 0.2 | 0.2 | 0.2 | 0–0.5 |
| Brightener 1 or 2 | 0.15 | 0.15 | 0.15 | 0.15 | 0–0.5 |
| Silicone antifoam | 0.12 | 0.12 | 0.12 | 0.12 | 0–0.3 |
| Fumed Silica | 0.0015 | 0.0015 | 0.0015 | 0.0015 | 0–0.003 |
| Perfume | 0.3 | 0.3 | 0.3 | 0.3 | 0–0.6 |
| Dye | 0.0013 | 0.0013 | 0.0013 | 0.0013 | 0–0.003 |
| Moisture/minors | Balance | Balance | Balance | Balance | Balance |
| Product pH (10% in DI water) | 7.7 | 7.7 | 7.7 | 7.7 | 6–9.5 |

What is claimed is:

1. A process for preparing modified alkylbenzenesulfonate surfactant suitable for use in cleaning products, said process comprising:
   (a) reducing the linearity of an olefin having molecular weight of at least about 126 and no more than about 280 by skeletally isomerizing, in the presence of a constrained skeletal isomerization catalyst, a substantially linear olefin preformed to have at least said molecular weight; and
   (b) a monoalkylation step having an internal isomer selectivity of from 0 to 40 comprising reacting the product of step (a) with an aromatic hydrocarbon selected from benzene, toluene and mixtures thereof in the presence of an alkylation catalyst.

2. A process according to claim 1 having the additional steps, of:
   (c) sulfonating the product of step-(b); and one or more steps selected from
   (d) neutralizing the product of step (c); and
   (e) mixing the product of step (c) or (d) with one or more cleaning product adjunct materials; thereby forming a cleaning product.

3. A cleaning product formed by the process of claim 2 and said process having both of said steps (d) and (e) in sequence and wherein said neutralization step is conducted using alkali selected from the group consisting of sodium, potassium, ammonium, magnesium and substituted ammonium alkalis and mixtures thereof.

4. A cleaning product formed by the process of claim 3 wherein said alkali is selected from the group consisting of sodium hydroxide, potassium hydroxide, ammonium hydroxide, sodium carbonate, potassium carbonate, and mixtures thereof.

5. A cleaning product formed by the process of claim 4 comprising:
   (a) from about 0.1% to about 50% of the product of step (d); and
   (b) from about 0.00001% to about 99.9% of one or more of said cleaning product adjunct materials.

6. A process according to claim 1 wherein aluminum chloride is substantially absent in step (b).

7. A process according to claim 1 wherein HF is substantially absent in step (b).

8. A process according to claim 1 wherein fluoridated zeolites are substantially absent in step (b).

9. A process according to claim 1 wherein said alkylation catalyst in step (b) is selected from shape-selective acidic zeolite-containing alkylation catalysts.

10. A process according to claim 9 wherein said zeolite in step (b) is selected from the group consisting of mordenite, ZSM-4; ZSM-12, ZSM-20, offretite, gmelinite and zeolite beta in at least partially acidic form.

11. A process according to claim 10 wherein the internal isomer selectivity in step (b) is from 0 to 20 and wherein said zeolite in step (b) is substantially in acid form and is contained in a catalyst pellet comprising a conventional binder and further wherein said catalyst pellet comprises at least about 1% of said zeolite.

12. A process according to claim 2 wherein said sulfonation step, (d), uses a sulfonating agent selected from sulfur trioxide, oleum, chlorosulfonic acid, and sulfuric acid.

13. A process according to claim 1 wherein step (a) is a skeletal isomerization step.

14. A process according to claim 13 wherein said constrained skeletal isomerization catalyst is selected from the group consisting of zeolites and aluminophosphates having one-dimensional pore structures with a pore size of from about 4.2 Angstrom to about 7 Angstrom.

15. A process according to claim 14 wherein said pore size is from about 5 to about 7 Angstrom.

16. A process according to claim 10 wherein the internal isomer selectivity in step (b) is from 0 to 10, said zeolite in step (b) is selected from said zeolite in substantially acid form and said zeolite in which at least 1% and not more than about 30% of the cationic sites are occupied by tin, platinum or mixtures thereof; said zeolite is contained in a catalyst pellet comprising a conventional binder, said catalyst pellet comprising at least about 50% of said zeolite, said zeolite has a primary crystal size of from about 0.1 to about 1 micron; said catalyst has a surface area of at least about 100 m$^2$/g, and said catalyst pellet is treated in a catalyst preactivation step comprising preheating said pellet at a temperature and pressure sufficient for removal of loosely bound water, ammonia and mixtures thereof.

17. A composition of matter consisting essentially of a member selected from the group consisting of modified alkylbenzenes, modified alkyltoluenes, modified alkylbenzenesulfonates and modified alkyltoluenesulfonates; wherein any of said members is the product of a process or method according to claim 1.

18. A process for preparing modified alkylbenzenesulfonate surfactant suitable for use in cleaning products, said process comprising
(a) a step of arriving at a reduced-linearity alkylating agent selected from an olefin having molecular weight, n, of at least about 126 and no more than about 280 and produced by a sequence of steps comprising:
   (i) skeletally isomerizing a linear paraffin having molecular weight of n+2 wherein n is said molecular weight of said olefin; and
   (ii) dehydrogenating the isomerized paraffin; and
(b) a monoalkylation step having an internal isomer selectivity of from 0 to 40 comprising reacting the product of step (a) with an aromatic hydrocarbon selected from benzene, toluene and mixtures thereof in the presence of an alkylation catalyst.

19. A process according to claim 18 having the additional steps, of
(c) sulfonating the product of step (b); and one or more steps selected from
(d) neutralizing the product of step (c); and
(e) mixing the product of step (c) or (d) with one or more cleaning product adjunct materials; thereby forming a cleaning product.

20. A cleaning product formed by the process of claim 19 and having both of said steps (d) and (e) in sequence and wherein said neutralization step is conducted using alkali selected from sodium, potassium, ammonium, magnesium and substituted ammonium alkalis and mixtures thereof.

21. A cleaning product formed by the process of claim 20 wherein said alkali is selected from sodium hydroxide, potassium hydroxide, ammonium hydroxide, sodium carbonate, potassium carbonate, and mixtures thereof.

22. A cleaning product formed by the process of claim 21 comprising:
(a) from about 0.1% to about 50% of the product of step (d); and
(b) from about 0.00001% to about 99.9% of one or more of said cleaning product adjunct materials.

23. A process according to claim 18 wherein aluminum chloride is substantially absent in step (b).

24. A process according to claim 18 wherein HF is substantially absent in step (b).

25. A process according to claim 18 wherein fluoridated zeolites are substantially absent in step (b).

26. A process according to claim 18 wherein said alkylation catalyst in step (b) is selected from shape-selective acidic zeolite-containing alkylation catalysts.

27. A process according to claim 26 wherein said zeolite in step (b) is selected from the group consisting of mordenite, ZSM-4, ZSM-12, ZSM-20, offretite, gmelinite and zeolite beta in at least partially acidic form.

28. A process according to claim 27 wherein the internal isomer selectivity in step (b) is from 0 to 20 and wherein said zeolite in step (b) is substantially in acid form and is contained in a catalyst pellet comprising a conventional binder and further wherein said catalyst pellet comprises at least about 1% of said zeolite.

29. A process according to claim 19 wherein said sulfonation step, (d), uses a sulfonating agent selected from sulfur trioxide, oleum, chlorosulfonic acid, and sulfuric acid.

30. A process according to claim 27 wherein the internal isomer selectivity in step (b) is from 0 to 10, said zeolite in step (b) is selected from said zeolite in substantially acid form and said zeolite in which at least 1% and not more than about 30% of the cationic sites are occupied by tin, platinum or mixtures thereof; said zeolite is contained in a catalyst pellet comprising a conventional binder, said catalyst pellet comprising at least about 50% of said zeolite, said zeolite has a primary crystal size of from about 0.1 to about 1 micron; said catalyst has a surface area of at least about 100 $m^2/g$, and said catalyst pellet is treated in a catalyst preactivation step comprising preheating said pellet at a temperature and pressure sufficient for removal of loosely bound water, ammonia and mixtures thereof.

31. A process according to claim 18 wherein the catalyst in step (a) (i) is a skeletal isomerization catalyst for paraffins selected from SAPO-11 and its derivatives and isotypes.

32. A process according to claim 18 wherein the catalyst in step (a) (ii) is a conventional dehydrogenation catalyst.

33. A process according to claim 18 wherein the catalyst in step (b) consists essentially of dealuminized H-mordenite.

34. A composition of matter consisting essentially of a member selected from the group consisting of modified alkylbenzenes, modified alkyltoluenes, modified alkylbenzenesulfonates and modified alkyltoluenesulfonates; wherein any of said members is the product of a process or method according to claim 18.

35. A method for improving the cleaning performance of a consumer cleaning product containing alkylarylsulfonate surfactant, said method comprising:
(a) at least one stage of delinearizing a (C10–C16 alkyl) arene to at least a minimum extent of about 0.1 methyl moieties per molecule of said alkylarene and a maximum extent of from about 1 to about 2.5 methyl moieties per molecule of said alkylarene, said stage comprising at least one linearity reduction step conducted prior to, in parallel with, or subsequent to, a step of coupling alkyl precursor and aryl precursor portions of said alkylarene;
(b) at least one step of sulfonating the alkylarene product of stage (a); and
(c) at least one step of formulating the alkylarylsulfonate surfactant product of step (b) in acid or salt form into a cleaning composition.

36. A method according to claim 35 wherein stage (a) forms 1-phenyl isomers of said alkylarene.

37. A method according to claim 35 wherein stage (a) forms 2-phenyl isomers of said alkylarene to an extent of at least about 60%.

38. A method according to claim 35 wherein stage (a) forms at least two homologs of said alkylarenes wherein said alkyl moieties bonded to said aryl moieties contain from 10 to 16 carbon atoms in total and wherein each of said homologs comprises at least two positional isomers with respect to the attachment of said methyl moieties to the balance of the alkyl moieties in said alkylarenes.

39. A method according to claim 35 wherein stage (a) is conducted without reliance on F-containing or aluminum chloride catalysts.

40. A method according to claim 35 wherein stage (a) is conducted without reliance on conventional strongly acid-catalyzed polymerization of propylene, such as HF- or Aluminum Chloride catalyzed polymerization.

41. A method according to claim 35 wherein more than 20% of the alkylarene molecules produced in stage (a) have one methyl moiety.

42. A method according to claim 35 wherein not more than about 20% of the alkylarene product molecules produced in stage (a) have two or more methyl moieties.

43. A method according to claim 35 wherein stage (a) includes a skeletal rearrangement step conducted after formation of said alkylarene.

44. A method according to claim 35 wherein stage (a) includes an isomerization step conducted in parallel with formation of said alkylarene.

45. A method according to claim 35 wherein stage (a) comprises Fischer-Tropsch chemistry and/or uses Synthol olefins.

46. A method according to claim 35 wherein stage (a) is independent of Fischer-Tropsch chemistry and/or is unreliant on Synthol olefins.

47. A method according to claim 35 wherein stage (a) includes use of a fluoride-free dealuminized mordenite catalyst.

48. A method according to claim 35 wherein stage (a) includes use of a ferrierite catalyst.

49. A method according to claim 35 wherein stage (a) produces a distribution of molecular weights consistent with presence in said alkylarylene of alkylarylene molecules having a total of carbon atoms including both odd and even carbon totals.

50. A cleaning composition produced by a method according to claim 35.

* * * * *